United States Patent
Stazzone et al.

(10) Patent No.: US 8,046,044 B2
(45) Date of Patent: Oct. 25, 2011

(54) METHOD AND APPARATUS FOR ACQUIRING OVERLAPPED MEDICAL IMAGE SLICES

(75) Inventors: Madelyn Milagros Stazzone, Chesterfield, MO (US); Omar G. El-Ghazzawy, St. Louis, MO (US); Fred William Prior, Town and Country, MO (US)

(73) Assignee: Washington University, St. Louis, MO (US)

( * ) Notice: Subject to any disclaimer, the term of this patent is extended or adjusted under 35 U.S.C. 154(b) by 1738 days.

(21) Appl. No.: 11/211,397

(22) Filed: Aug. 25, 2005

(65) Prior Publication Data
US 2006/0079755 A1   Apr. 13, 2006

Related U.S. Application Data

(60) Provisional application No. 60/604,214, filed on Aug. 25, 2004, provisional application No. 60/679,561, filed on May 10, 2005.

(51) Int. Cl.
*A61B 5/05* (2006.01)
(52) U.S. Cl. ......... 600/407; 600/410; 324/307; 324/309
(58) Field of Classification Search ............. 600/407, 600/410, 417; 324/307, 309
See application file for complete search history.

(56) References Cited

U.S. PATENT DOCUMENTS

| 5,167,232 A * | 12/1992 | Parker et al. ............. 600/419 |
| 6,600,317 B1 * | 7/2003 | Kumai et al. ............. 324/307 |
| 2004/0252870 A1 | 12/2004 | Reeves et al. |
| 2005/0151538 A1 | 7/2005 | Ichinose et al. |

OTHER PUBLICATIONS

Kleinheinz et al., "Three-dimensional magnetic resonance imaging of the orbit in craniofacial malformations and trauma", Int. J. Adult Orthodon Orthognath Surg., 2000, Spring;15(1):64-68.
Klingebiel et al., "Three-dimensional Imaging of the Inner Ear by Volume-Rendered Reconstructions of Magnetic Resonance Data", Arch Otolaryngol Head Neck Surg., May 2002;128(5):549-553.
Krombach et al, "MRI of the Inner Ear: Comparison of Axial T2-Weighted, Three-Dimensional Turbo Spin-Echo Images, Maximum-Intensity Projections, and Volume Rendering", Invest. Radiol., Jun. 2000;35(6):337-342.
Lee et al., "Volumetric MR Imaging of the Liver and Applications", Magn. Reson. Imaging Clin. N. Am., Nov. 2001;9(4):697-716.
McKinnon et al., "Ultra-Fast Imaging Using an Interleaved Gradient Echo Planar Sequence", Books of Abstracts, 11th Annual Meeting, Society of Magnetic Resonance in Medicine, p. 106 (1992).
Phillips et al., "Temporal Lobe Activation Demonstrates Sex-based Differences during Passive Listening", Radiology, Jul. 2001;220(1):202-207.
Sailhan et al., "Three-dimensional MR imaging in the assessment of physeal growth arrest", Eur. Radiol., Sep. 2004;14(9):1600-1608.

(Continued)

*Primary Examiner* — Brian Casler
*Assistant Examiner* — Nasir Shahrestani
(74) *Attorney, Agent, or Firm* — Thompson Coburn LLP

(57) ABSTRACT

The disclosure describes a technique for medical imaging, referred to herein as the Rapid Interleave Overlap Technique (RIOT), wherein image data is acquired as a plurality of series sequences in a manner that allows for unlimited overlap. RIOT involves interleaving and overlapping 2D image slices of multiple series of image data of the same ROI into a composite data set from which MPR and 3D reconstructions exhibiting excellent resolution properties and crisp image quality can be generated.

42 Claims, 20 Drawing Sheets

OTHER PUBLICATIONS

Patent Cooperation Treaty; Notification of Transmittal of the International Search Report and the Written Opinion of the International Searching Authority, or the Declaration; International Application No. PCT/US05/30480; International Filing Date: Aug. 25, 2005.

Haacke et al., "One-Dimensional Fourier Imaging, k-Space and Gradient Echoes", Magnetic Resonance Imaging, Physical Principles and Sequence Design, Chapter 9, 1999, pp. 139-163.

Haacke et al., "Signal, Contrast and Noise", Magnetic Resonance Imaging, Physical Principles and Sequence Design, Chapter 15, 1999, pp. 331-380.

Haacke et al., "A Closer Look at Radiofrequency Pulses", Magnetic Resonance Imaging, Physical Principles and Sequence Design, Chapter 16, 1999, pp. 381-419.

Haacke et al., "Fast Imaging in the Steady State", Magnetic Resonance Imaging, Physical Principles and Sequence Design, Chapter 18, 1999, pp. 451-512.

Haacke et al., "Segmented k-Space and Echo Planar Imaging", Magnetic Resonance Imaging, Physical Principles and Sequence Design, Chapter 19, 1999, pp. 513-568.

Haacke et al., "Magnetic Field Inhomogeneity Effects and T2* Dephasing", Magnetic Resonance Imaging, Physical Principles and Sequence Design, Chapter 20, 1999, pp. 569-617.

Haacke et al., "Sequence Design, Artifacts and Nomenclature", Magnetic Resonance Imaging, Physical Principles and Sequence Design, Chapter 26, 1999, pp. 781-825.

\* cited by examiner

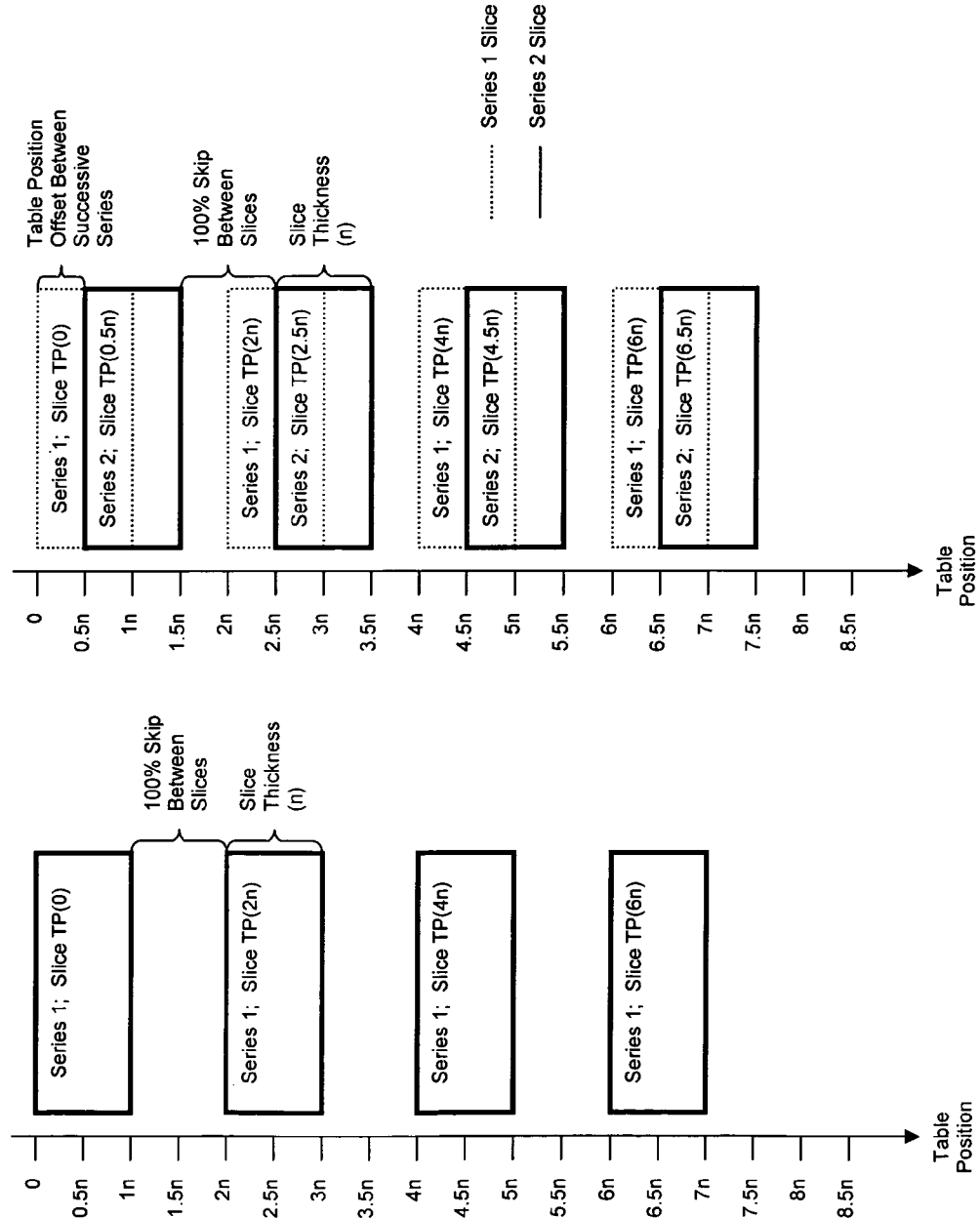

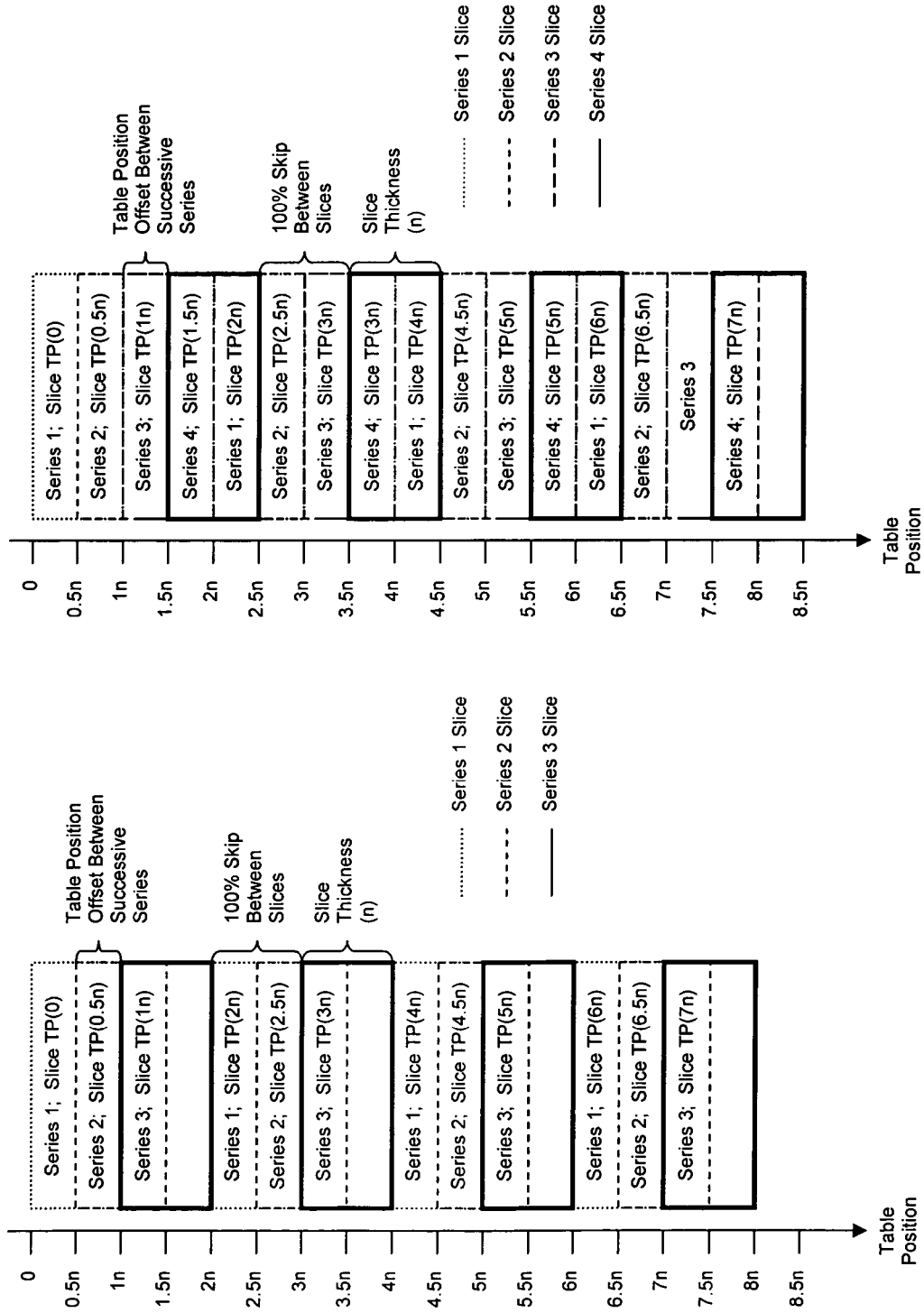

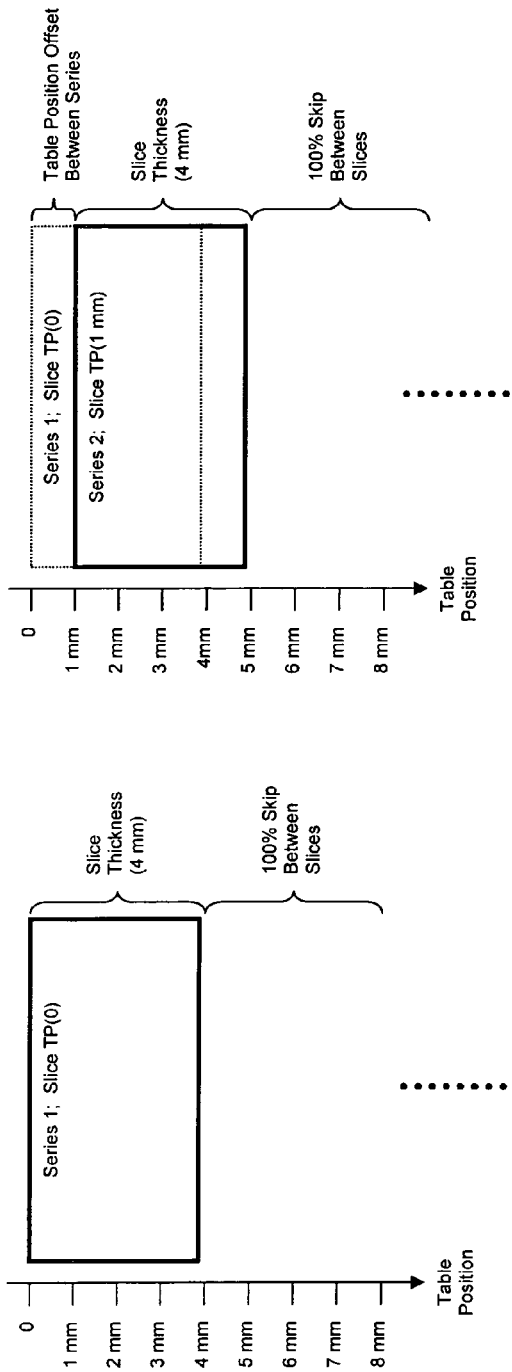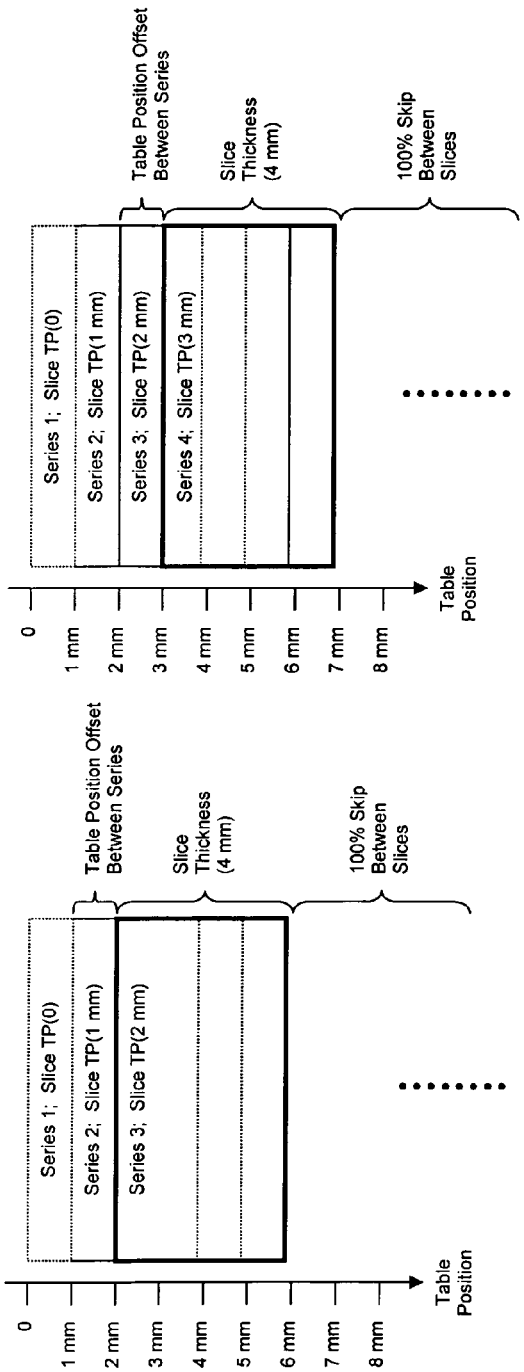
Figure 4(a)
Figure 4(b)
Figure 4(c)
Figure 4(d)

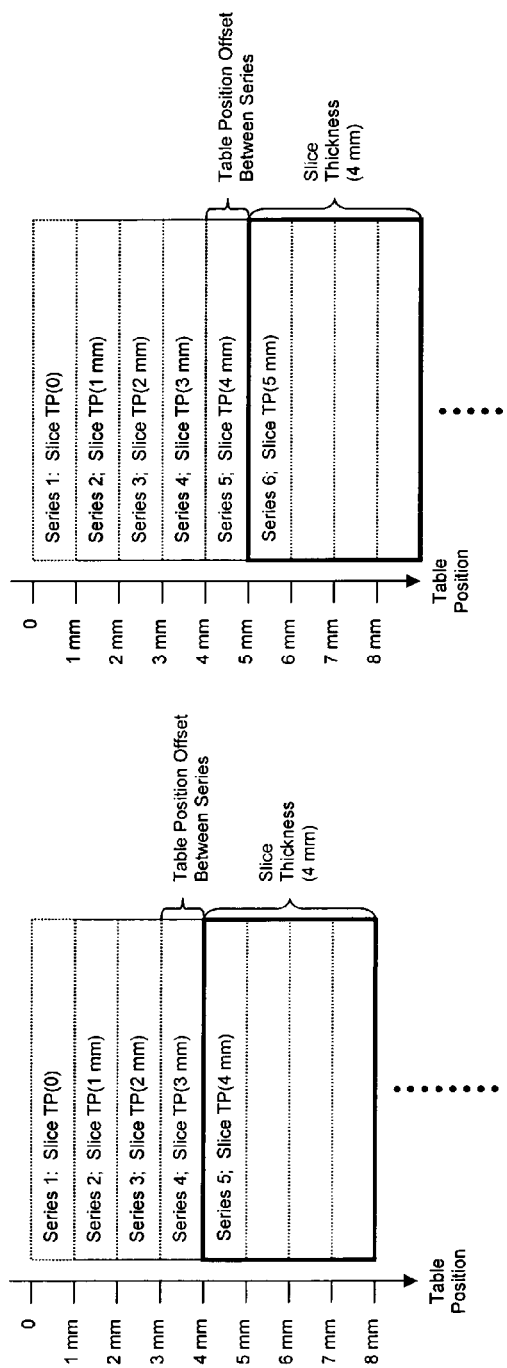
Figure 4(e)
Figure 4(f)
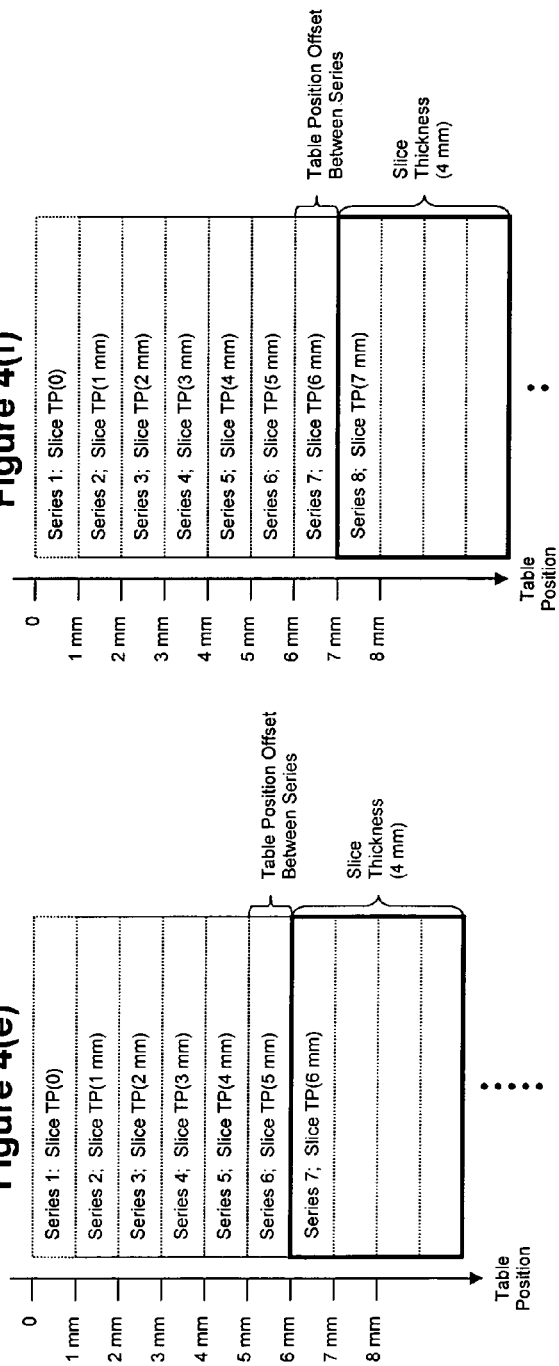
Figure 4(g)
Figure 4(h)

METHOD AND APPARATUS FOR ACQUIRING OVERLAPPED MEDICAL IMAGE SLICES

CROSS REFERENCE AND PRIORITY CLAIM TO RELATED APPLICATIONS

This application claims priority to provisional patent application Ser. Nos. 60/604,214 filed Aug. 25, 2004, entitled "Method and Apparatus for Acquiring Overlapped Medical Image Slices" and 60/679,561, filed May 10, 2005, entitled "Method and Apparatus for Acquiring Overlapped Medical Image Slices", the entire disclosures of both of which are incorporated herein by reference.

FIELD OF THE INVENTION

The present invention relates to medical imaging, in particular magnetic resonance (MR) imaging and computed tomography (CT) imaging.

BACKGROUND OF THE INVENTION

Multi-planar (MPR) and three-dimensional (3D) reconstructions of two-dimensional (2D) image slice data can be very helpful to clinicians, particularly in connection with surgical planning. However, current MR imaging techniques for acquiring medical image slices of a patient's region of interest (ROI) are of limited value when high quality MPR and 3D reconstructions are desired. In MR, the slice thickness for a given acquisition is constrained by multiple factors such as sequence, specific absorption rate (SAR) and field of view (FOV). In addition, in MR there is only one "detector," the coil unit (e.g., the head coil). Since there is only one detector with MR imaging (unlike CT imaging, wherein multi-detector CT scanners can use several detectors to simultaneously acquire image data), acquisition parameters such as base resolution and slice thickness have much more of a direct impact on acquired images. This limits the ability to change parameters readily before and after image acquisition. In MR there is always a trade-off. For example, although a smaller slice thickness will yield better resolution, smaller slice thickness will also result in decreased signal to noise (SNR), thereby leading to increased scan time and SAR. Each sequence therefore has an allowable slice thickness range. In addition, as the slice thickness decreases, other factors such as "cross-talk" may increase, thereby further reducing image quality. This in turn limits the ability to overlap slice information, a problem that has plagued conventional high resolution MR MPR and 3D reconstruction techniques.

In order to produce high quality MPR and 3D images, an overlap of 50% is desirable. For the reasons stated above, traditional MR techniques do not allow for this degree of overlap of 2D images. Currently, the best MR techniques available for generating 3D images are believed to be volumetric acquisitions, where the base image resolution can be quite good. However, as stated above, with the increase in resolution for such techniques, the SNR is decreased, with the end result being that even the most optimal 3D MR sequence cannot compare to the 3D images derived by current multi-detector CT technology. 3D reconstructions derived from 2D MR acquisitions are even more limited. These images, which have limited resolution and poor SNR, do not produce 3D volumetric images with the quality required for many diagnostic assessments.

Additional background information pertaining to MR imaging issues can be found in the following publications, the entire disclosures of each of which are incorporated herein by reference: Sailhan F, Chotel F, Guibal A L, Gollogly S, Adam P, Berard J, Guibaud L: *Three-dimensional MR imaging in the assessment of physeal growth arrest*, European Radiology, 2004; April 3 [Epub ahead of print]; Klingebiel R, Thieme N, Kivelitz D, Enzweiler C, Werbs M, Lehmann R: *Three-dimensional imaging of the inner ear by volume-rendered reconstructions of magnetic resonance data*, Archives of Otolaryngology Head and Neck Surgery, 2002; 128:549-53; Lee V S, Lavelle M T, Krinsky G A, Rofsky N M: *Volumetric MR imaging of the liver and applications*, Magnetic Resonance Imaging Clinics of North America, 2001; 9:697-716; Kleinheinz J, Stamm T, Meier N, Wiesmann H P, Ehmer U, Joos U: *Three-dimensional magnetic resonance imaging of the orbit in craniofacial malformations and trauma*, International Journal of Orthodontic Orthognath Surgery 2000; 15:64-8; Krombach G A, Schmitz-Rode T, Tacke J, Glowinski A, Nolte-Ernsting C C, Gunther R W: *MRI of the inner ear: comparison of axial T2-weighted, three-dimensional turbo spin-echo images, maximum-intensity projections, and volume rendering*, Investigational Radiology, 2000; 35:337-42; McKinnon G C, Eichenberger A C, von Weymarn C A, von Schulthess G K; *Ultrafast imaging using an interleaved gradient echo planar sequence in Books of Abstracts*, 11$^{th}$ Annual Meeting, Society of Magnetic Resonance in Medicine, 1992; 106; Phillips M D, Lowe M J, Lurito J T, Dzemidzic M, Mathews V P: *Temporal lobe activation demonstrates sex-based differences during passive listening; Radiology,* 2001; 220:202-07; and Haacke E. M., Brown R. W., Thompson M. R. and Venkatesan R.: *Magnetic Resonance Imaging Physical Principles and Sequence Design*, John Wiley & Sons, 1999.

SUMMARY OF THE INVENTION

A goal of the present invention is to provide a solution to the shortcomings discussed above. In accordance with one aspect of the preferred embodiment of the present invention, image data is acquired as a plurality of series sequences in a manner that allows for unlimited overlap. This technique, which will be described in greater detail below, is referred to herein as the Rapid Interleave Overlap Technique (RIOT).

The RIOT technique involves interleaving and overlapping 2D image slices of multiple series of image data of the same ROI into a composite data set from which MPR and 3D reconstructions exhibiting excellent resolution properties and crisp image quality can be generated. It is also believed that the image slices within the composite data set can be segmented into thinner slices. Starting from an initial position in a scanner's coordinate system (preferably an initial table position), the RIOT technique comprises acquiring an image data series, wherein the image data series comprises a plurality of image slices having a specified slice thickness and a specified skip therebetween. After this series is acquired, the initial table position is reset to new value offset by an amount determined as a function of the desired degree of overlap for the resultant aggregated image. Next, starting from this new initial table position, another image data series is acquired with the same slice thickness and skip parameters as the previous series. Thereafter, depending upon the desired degree of overlap, the initial table position is adjusted again and yet another image data series with the same slice thickness and skip parameters as the previous series is acquired, albeit starting from the new initial table position. If an overlap of 50% is desired, four series will preferably be acquired. If an overlap of 100%, eight series will preferably be acquired.

After all of the image data series have been acquired, the image slices of these series can be assembled into a composite data set. The image slices within the composite data set are preferably sorted by slice position (table position) and re-ordered within the composite data set by ascending or descending slice position (table position). Also disclosed herein is an automated software program configured to perform this sorting operation.

With RIOT, "cross-talk" between image slices can be virtually eliminated so that excellent SNR can be maintained even though images are segmented at effectively smaller slice thicknesses than the original image slices of the original data series. Furthermore, multiple series can be interleaved with as large of an overlap as is needed, even as high as 100%. In other words, RIOT allows for essentially an unlimited amount of user-configurable overlap, a feature not believed to be possible even with current CT technology. Experimentation with RIOT indicates that an overlap of 50% will yield excellent MPRs and 3D reconstructions with enhanced image detail.

Also, in addition to the option of the acquiring image slices in the standard axial, sagittal, and a coronal planes, it is preferred that the present invention also be configured to allow for the acquisition of image slices in planes of any obliquity.

These and other features and advantages of the present invention are set forth below and in the enclosed figures.

BRIEF DESCRIPTION OF THE DRAWINGS

FIGS. 3(a)-(d) illustrate an exemplary application of the present invention wherein 4 series of image slices are acquired to obtain a 50% overlap;

FIGS. 4(a)-(h) illustrate an exemplary application of the present invention wherein 8 series of 4 mm image slices are acquired to obtain a 100% overlap;

DETAILED DESCRIPTION OF THE PREFERRED EMBODIMENTS

Figure 1:
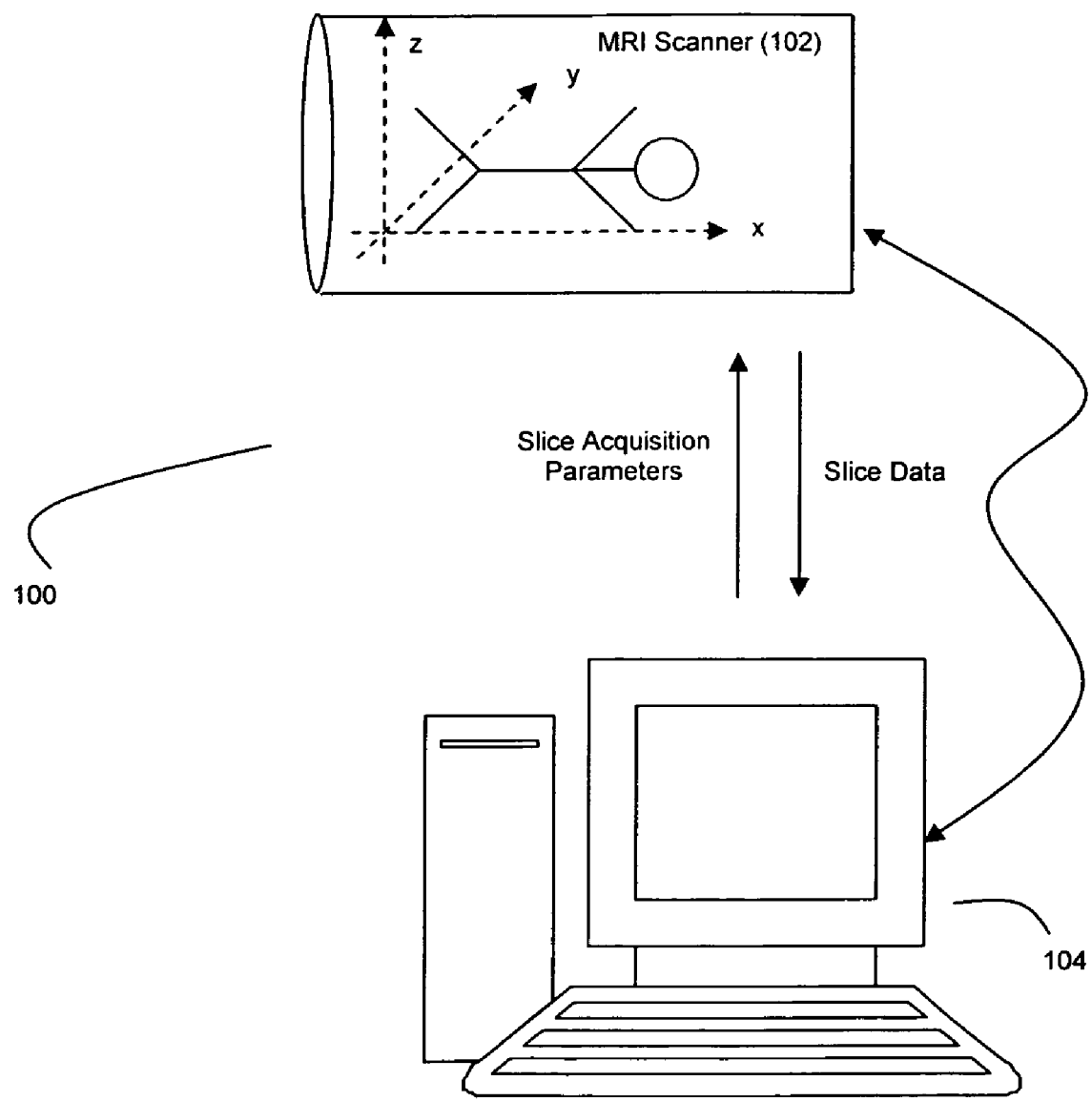
FIG. 1 depicts an overview of a preferred image data acquisition system in which the present invention is implemented.

FIG. 1 illustrates a preferred image data acquisition system 100 in accordance with the teachings of the present invention. An MR scanner 102 is used to acquire 2D image data corresponding to a patient's ROI along selected ones of the xy (coronal), xz (sagittal), and yz (axial) planes. If desired, 2D image data can also be obtained in planes of other specified obliquities. The scanner 102 acquires 2D image slices in accordance with instructions provided by a clinician via a scanner interface control computer 104. Through control computer 104, a clinician can specify the necessary slice parameters for a given acquisition, as is readily understood in the art. The resultant image data acquired by the scanner 102 are then returned to control computer 104 for further processing thereby. A preferred system 100 suitable for use with the present invention is a 1.5 Tesla Siemens Sonata Magnetom System manufactured by Siemens Medical Systems of Erlangen, Germany. It should be understood, however, that other image data acquisition systems can be used in the practice of the present invention. Furthermore, the technique of the present invention is believed to be suitable for use with any type of coil unit.

Figure 2:
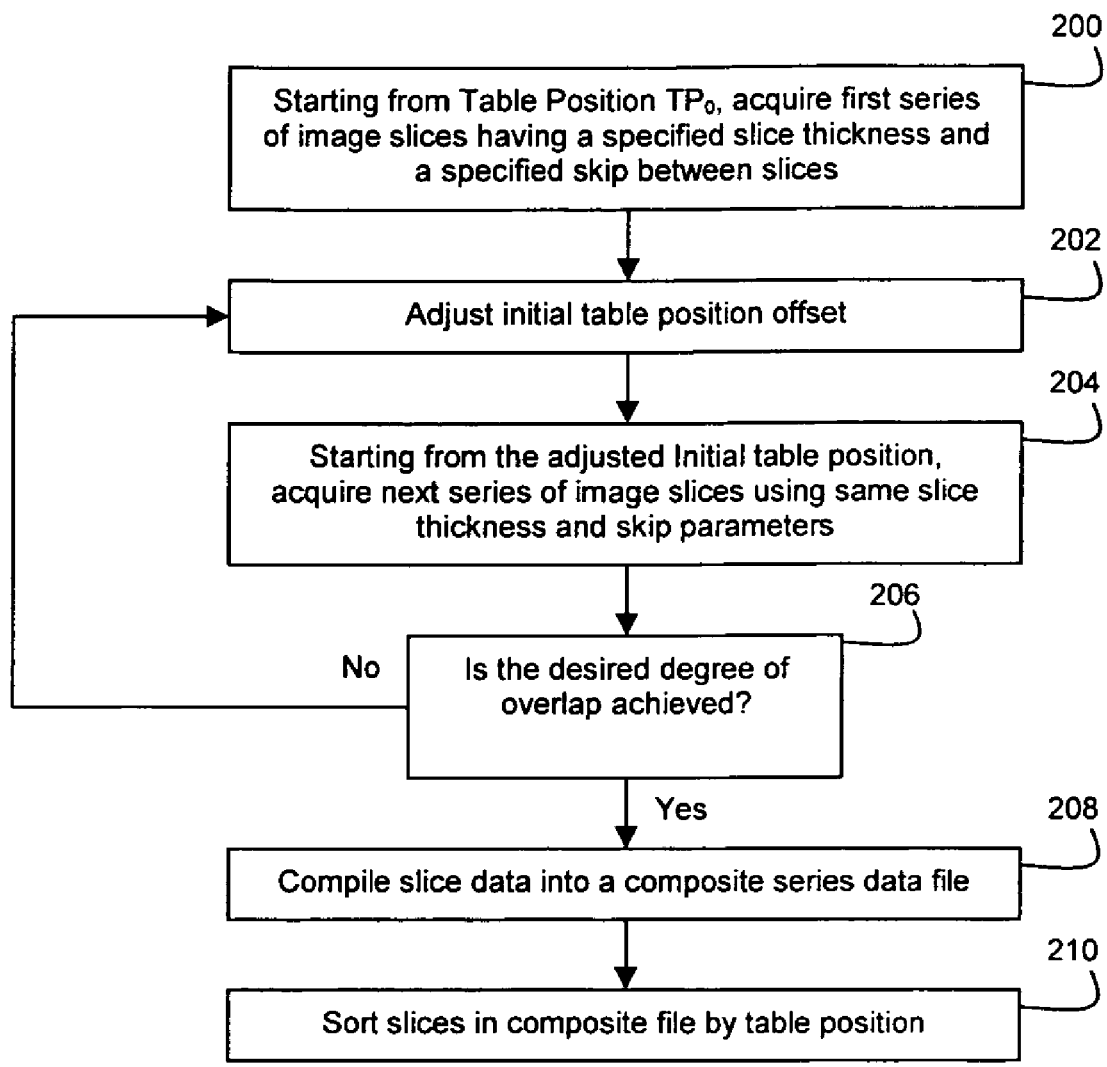
FIG. 2 is a flowchart illustrating a preferred implementation of the present invention.
Figure 5A:
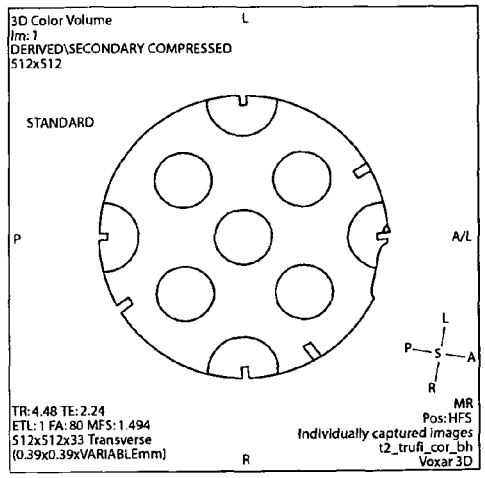
FIGS. 5(a)-(d) illustrate various 3D reconstructions of phantom images.
Figure 5B:
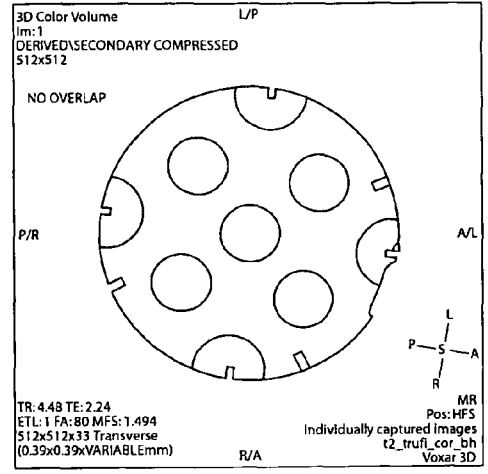
Figure 5C:
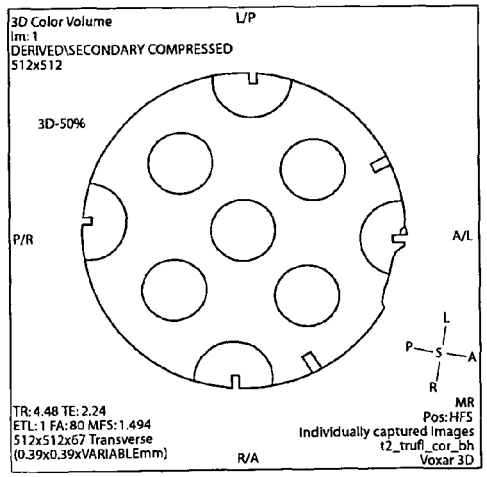
Figure 5D:
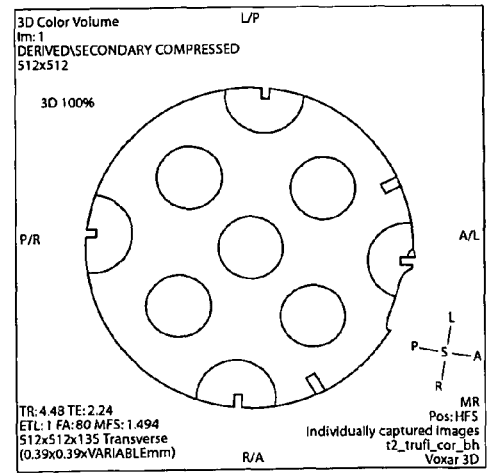

The present invention arises in the manner by which the scanner acquires image data. FIG. 2 is a flowchart illustrating this process, which can be applied to any 2D sequence. With RIOT, the slice acquisition parameters for each acquired series are the same except for table position (TP). The field of view (FOV) can be set at 100%, but phase over sampling may be used so long as it is identical for all series sequences. Fat saturation may also optionally be used. Furthermore, the average (NEX) can be set to one (or can be multiple so long as each image data series has the same number of averages). The skip between image slices is set to 100%. It is also strongly preferred that the plane of acquisition be the same as the desired plane of the multi-planar or 3D reconstruction, as the resolution is believed to be best in the plane of acquisition. For instance, if the desired 3D representation or MPR is in the coronal plane, then the series should be acquired coronally. Earlier experiments had suggested that in order to achieve adequate interleaving the plane of each series sequence had to be defined relative to the table and not the ROI being scanned. For example, these earlier experiments suggested that the coronal plane should be defined off of an axial image by lines running parallel to the "X" axis of the axial localizer. In other words images were to be acquired in the axial, sagittal or coronal plane relative to the table itself, not the anatomy being imaged. However, later experiments have determined that the plane of acquisition can be prescribed in any obliquity.

Experimentation also indicates that an original slice thickness of 4 mm is optimal for reasons that will discussed below. 4 mm is the preferred original slice thickness because an original slice thickness below 4 mm would complicate the mathematical calculations without significant change in scan times. Also, because the ultimate slice thickness is primarily the result of the number of series that are interleaved, a thinner original slice thickness will not have a significant effect in terms of the thickness of the resultant composite series. For example, If 4 series of 4 mm thick slices are interleaved and overlapped by 50%, the resultant composite series will have a 2 mm slice thickness. If 4 series of 3 mm slices are interleaved and overlapped by 50%, the resultant composite series will have a 1.5 mm slice thickness. Nevertheless, if necessary, slice thicknesses thinner or thicker than 4 mm can be used and are also suitable for the practice of the present invention.

With reference to FIG. 2, at step 200, the scanner 102 acquires a first image data series starting from table position TP(0). It is worth noting that it is believed to be best to start with the TP dictated by the scanner rounded off to the nearest whole number, in which case TP(0) can be thought of as whatever the starting table position dictated by the scanner is. However, other starting table positions may optionally be used. Furthermore, experimentation shows that setting the TP of the first series at true 0 or close to true 0 can result in errors. However, it is believed that this can be remedied by an automated software program as described below. FIG. 3(a) illustrates an example of the result of this step, wherein four image slices of thickness n mm are acquired starting at TP(0 mm)

with a 100% skip therebetween (i.e., a skip of n mm). While the example of FIGS. 3(a)-(d) depict the acquisition of four slices per series, it should be understood that more or fewer slices can be acquired each sequence.

A skip of 100% is strongly preferred because a skip of less than 100% would require that each series have a different skip in order to achieve a desired overlap. For instance, theoretically, a 50% overlap can also be achieved by interleaving 3 series instead of 4. In this setting, Series A (with a slice thickness of 4 mm, TP (0) and skip of 100%) would have to be overlapped with series B (slice thickness, 4 mm, TP (4) and skip of 100%. This is possible and would yield a composite series with 4 mm slices and 0 skip. However, in order to achieve a 50% skip with only 3 series, the third series would have to have a TP of (2) and a skip of 50%. Accordingly, to accommodate a skip not equal to 100%, special software would have to be designed to accommodate interleaving of the slices. In addition, another problem arising from the use of a skip less than 100% is the "cross-talk" which may result, thereby causing a degradation of signal to noise ratio.

After the first series is acquired, the starting table position for the next series is then adjusted (step 202). Starting table position adjustments between series will be based on fractions of the original slice thickness as determined by a desired degree of overlap. The starting table position of the next series is preferably adjusted by n/k mm, wherein the value of k depends upon the desired degree of overlap. If a 50% overlap is desired, k is preferably 2. If a 100% overlap is desired, k is preferably 4. A slice thickness of 4 mm, facilitates these calculations as it will result in TP adjustments in whole numbers rather than in fractional increments. However, as noted above and below, where automated software is utilized to perform table position adjustments, this concern is attenuated.

While the examples of FIGS. 3(a)-(d) and 4(a)-(h) depict the starting table position being incremented by n/k mm for each series, it should be readily understood that the starting table position can also be decremented by n/k mm for each series. Again, experimentation with the Siemens scanner shows that decrementing will not always work if the starting TP of the first series is set at true 0 or slightly greater or less than true 0. The reason for this is that in this setting some of the series will require a starting TP of a positive value, while others will require a starting TP which is of a negative value. This will result in errors with interleaving by the control computer. Again, it is possible, however, that this problem can be remedied via a dedicated software program.

Table position (TP) shifts can be adjusted in any obliquity. However, with the preferred RIOT technique, all TP adjustments must be made in the same direction for a given set of acquisitions (either positive or negative), defined by the plane of the acquisition. As stated above, experiments show that the resolution of the 3D or MPR reconstruction is optimal when the plane of the acquisition is in the desired plane of the 3D or MPR reconstruction.

Figure 8A:
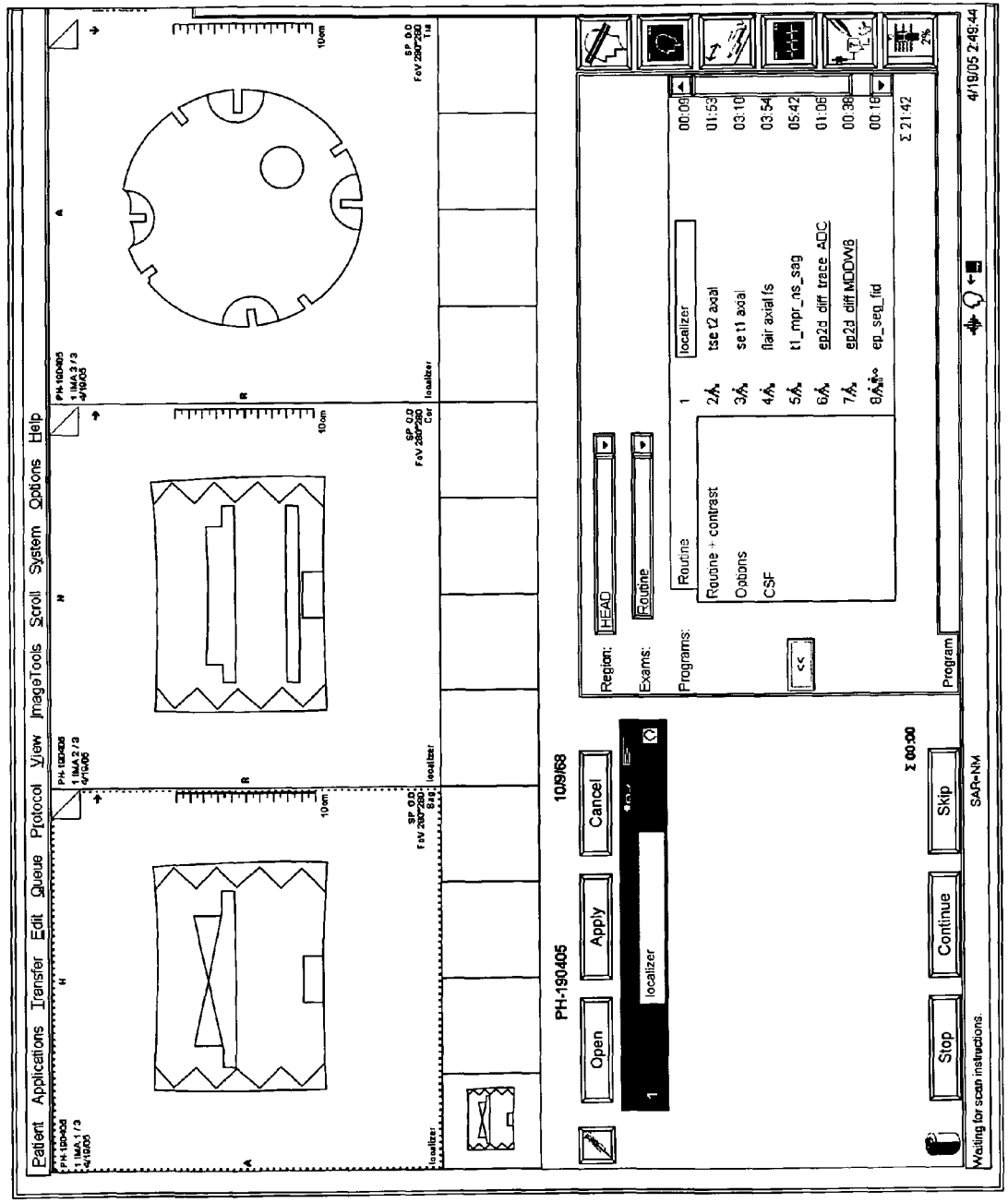
FIGS. 8(a)-(k) illustrate a sequence of screenshots illustrating how a series of image slices can be acquired in any obliquity.
Figure 8B:
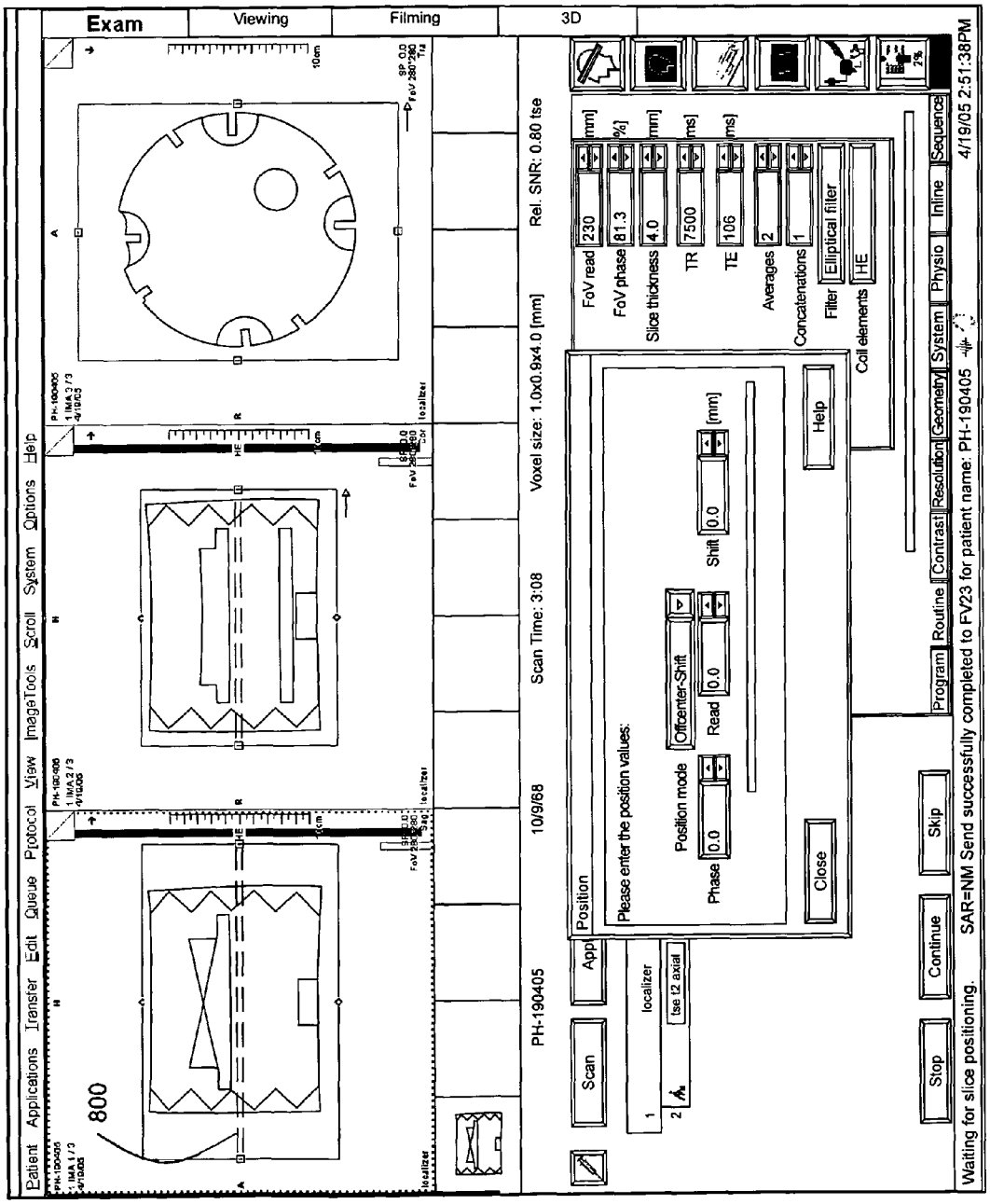
Figure 8C:
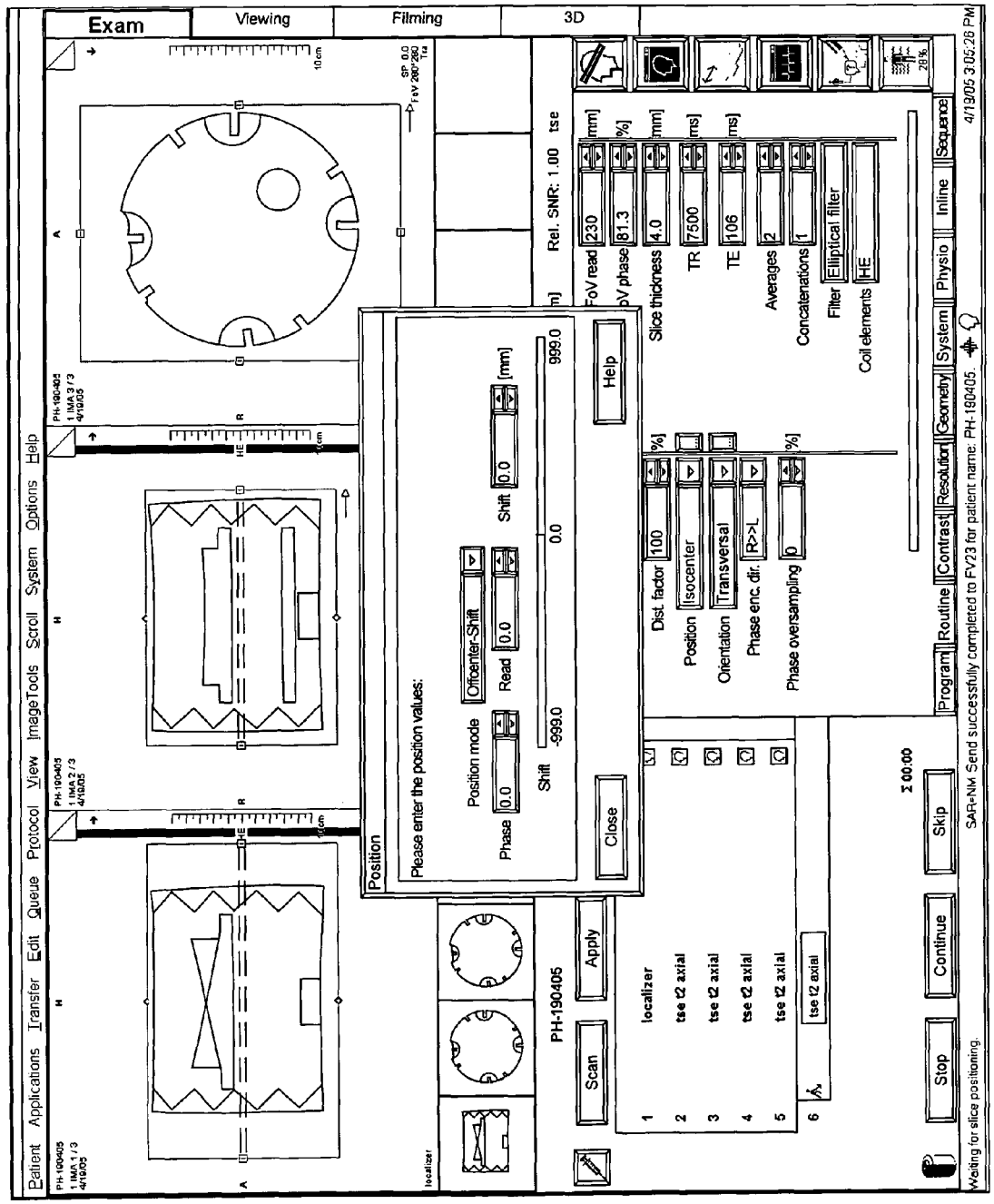
Figure 8D:
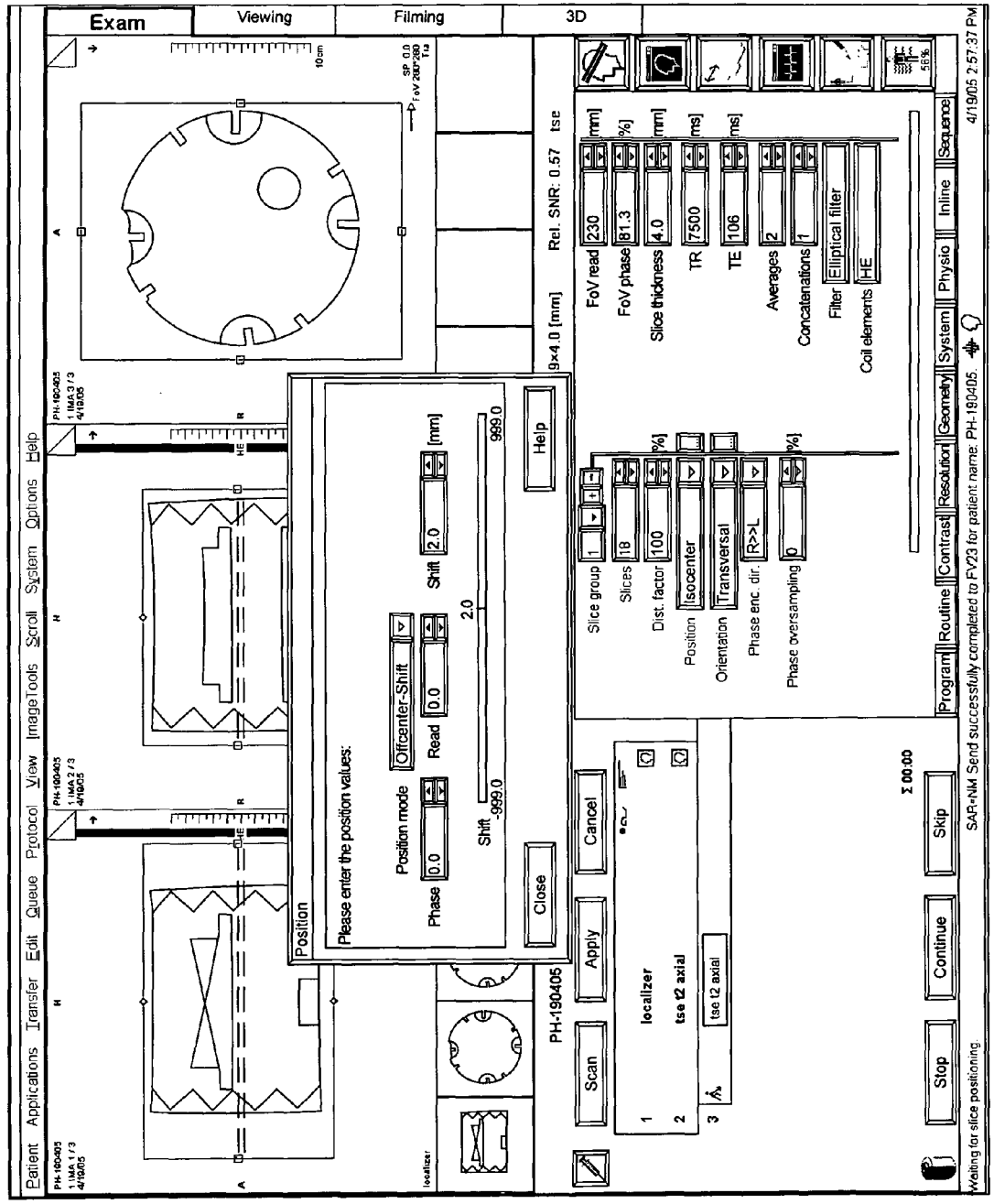
Figure 8E:
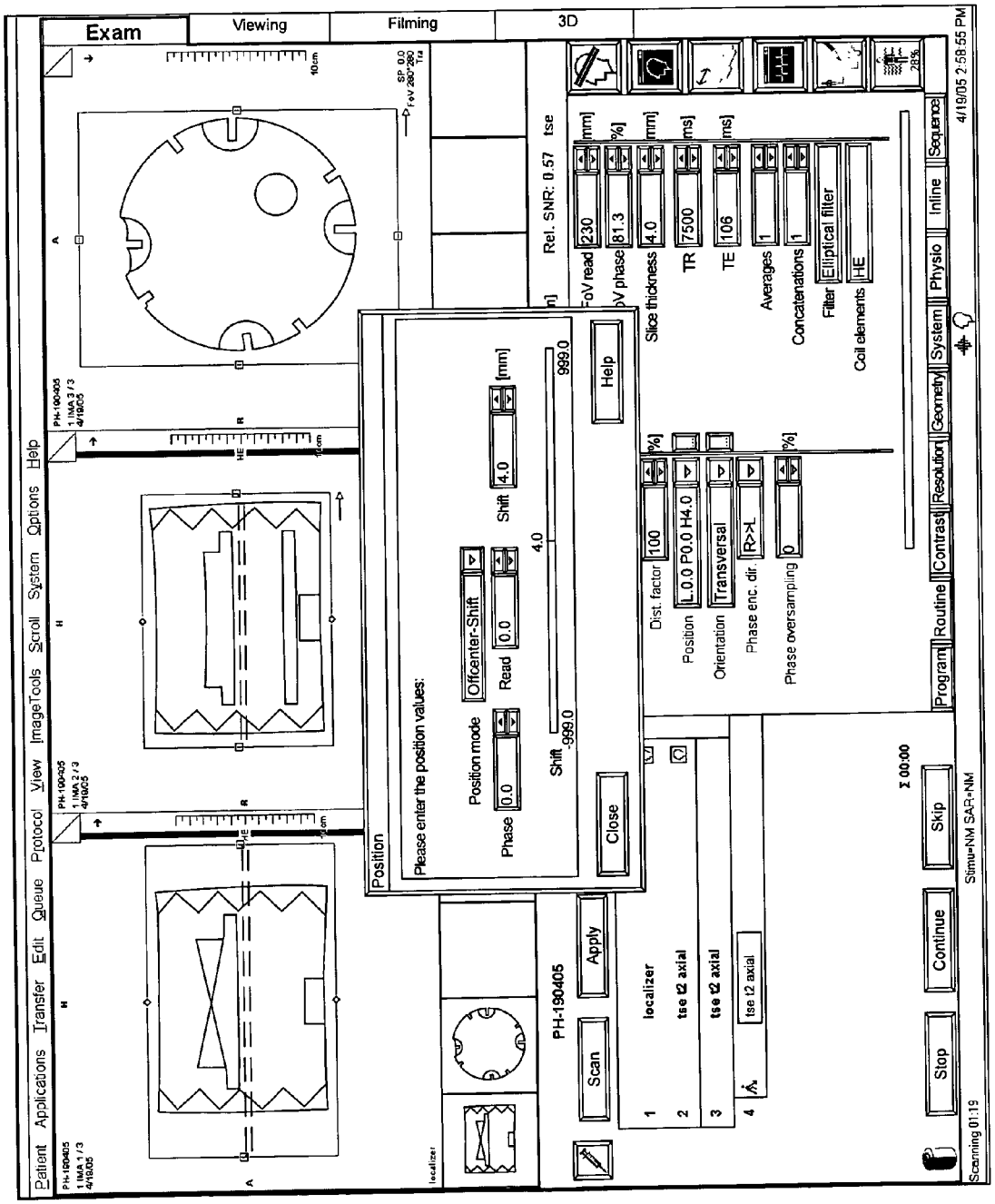
Figure 8F:
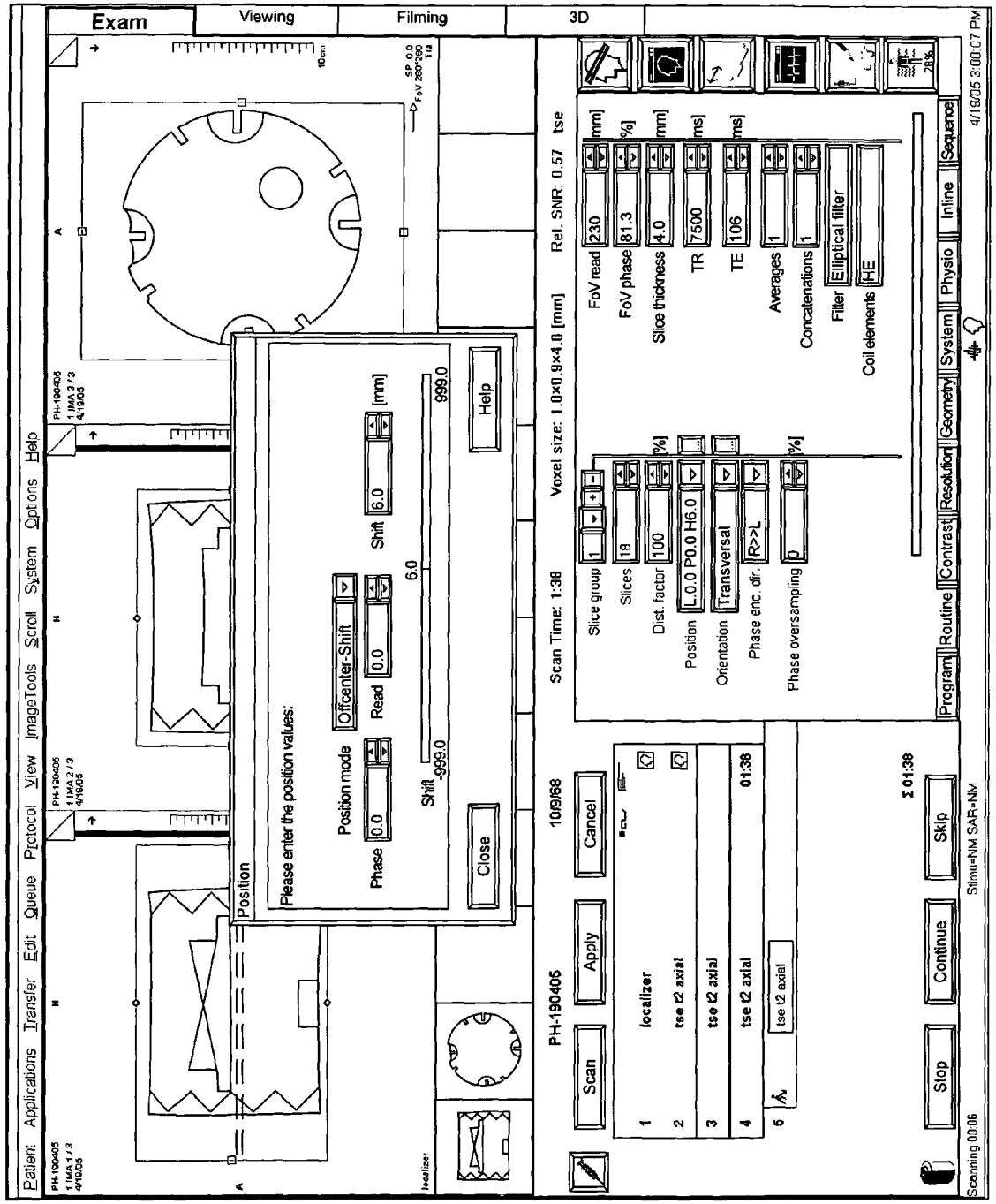
Figure 8G:
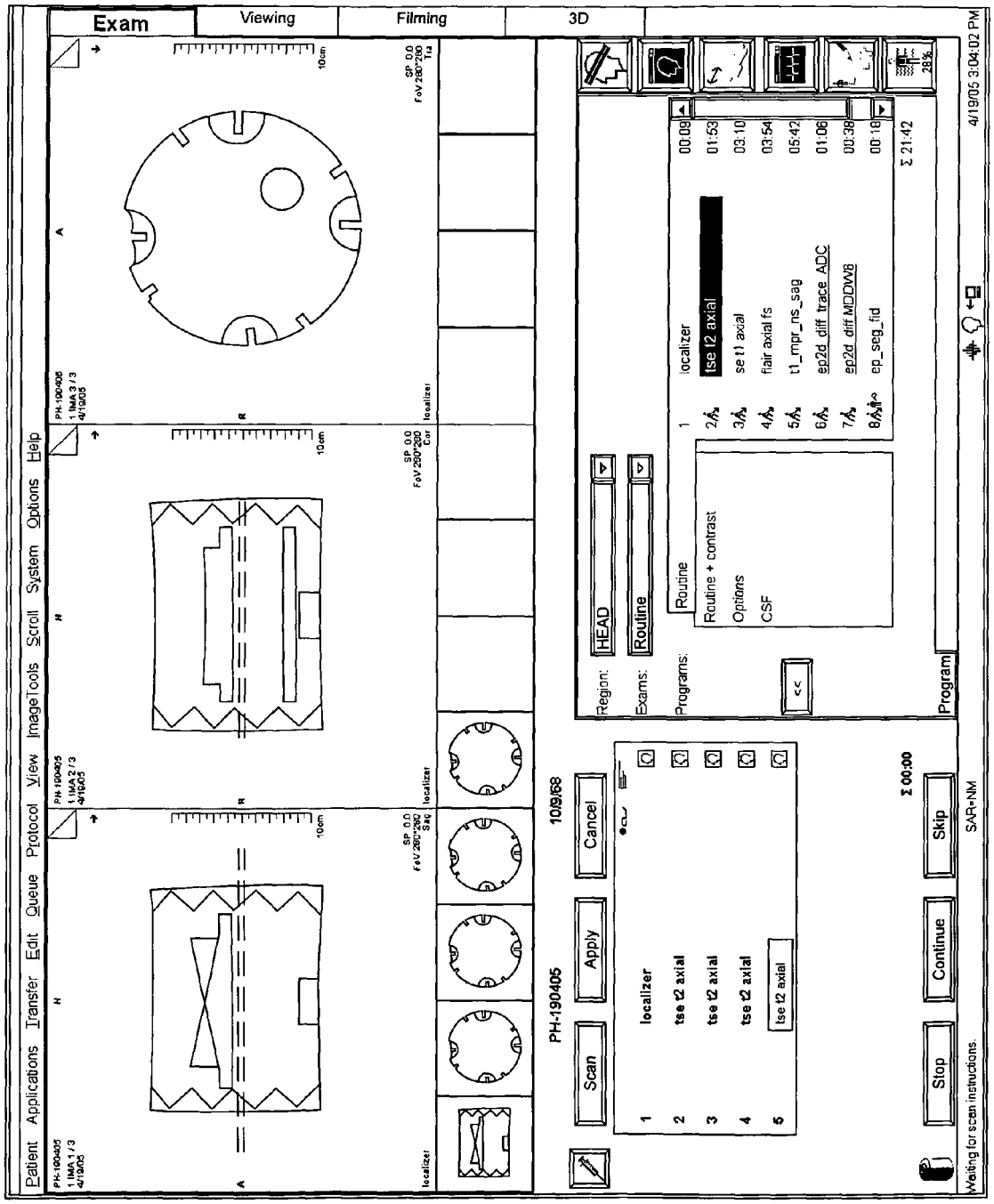
Figure 8H:
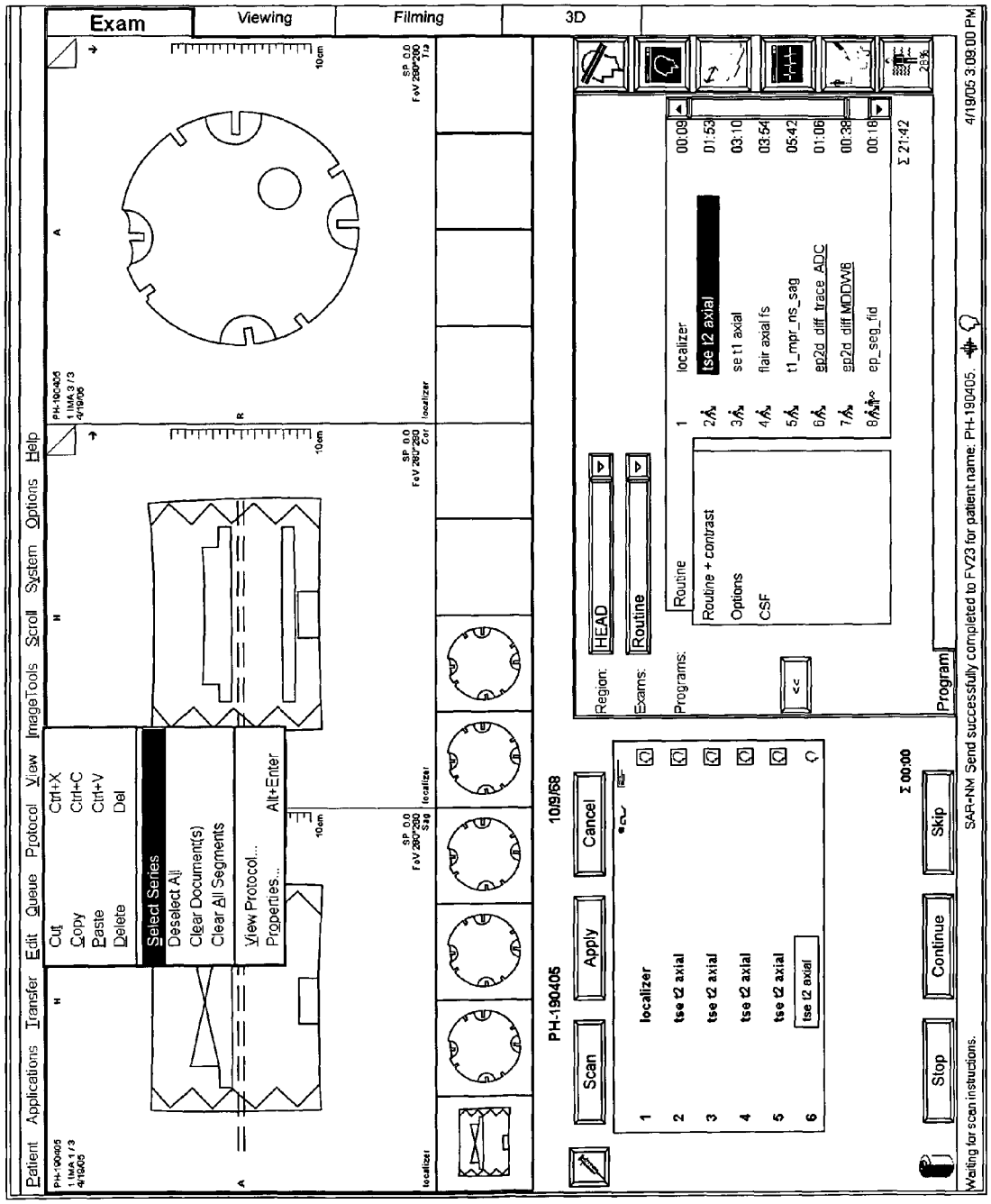
Figure 8I:
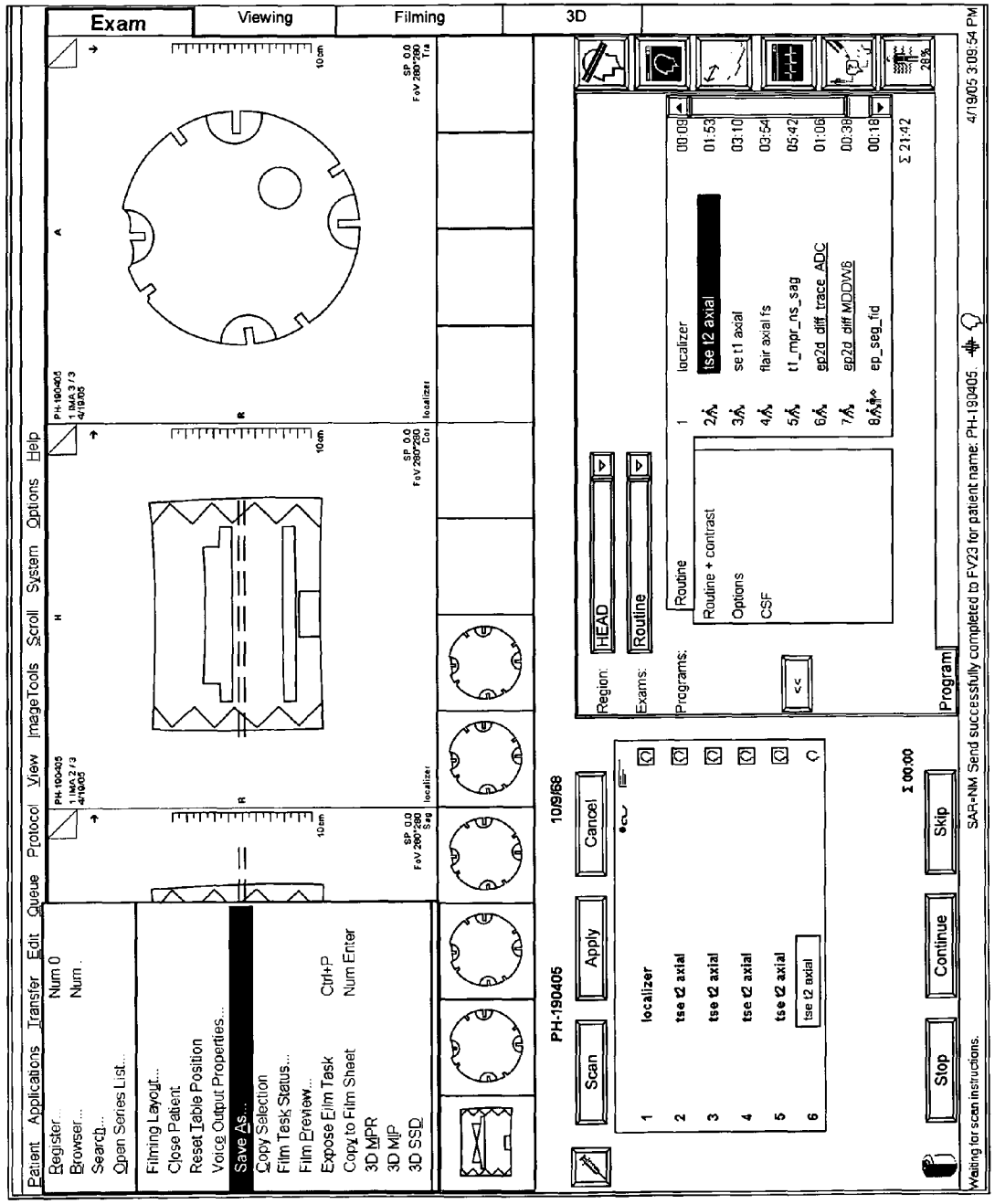
Figure 8J:
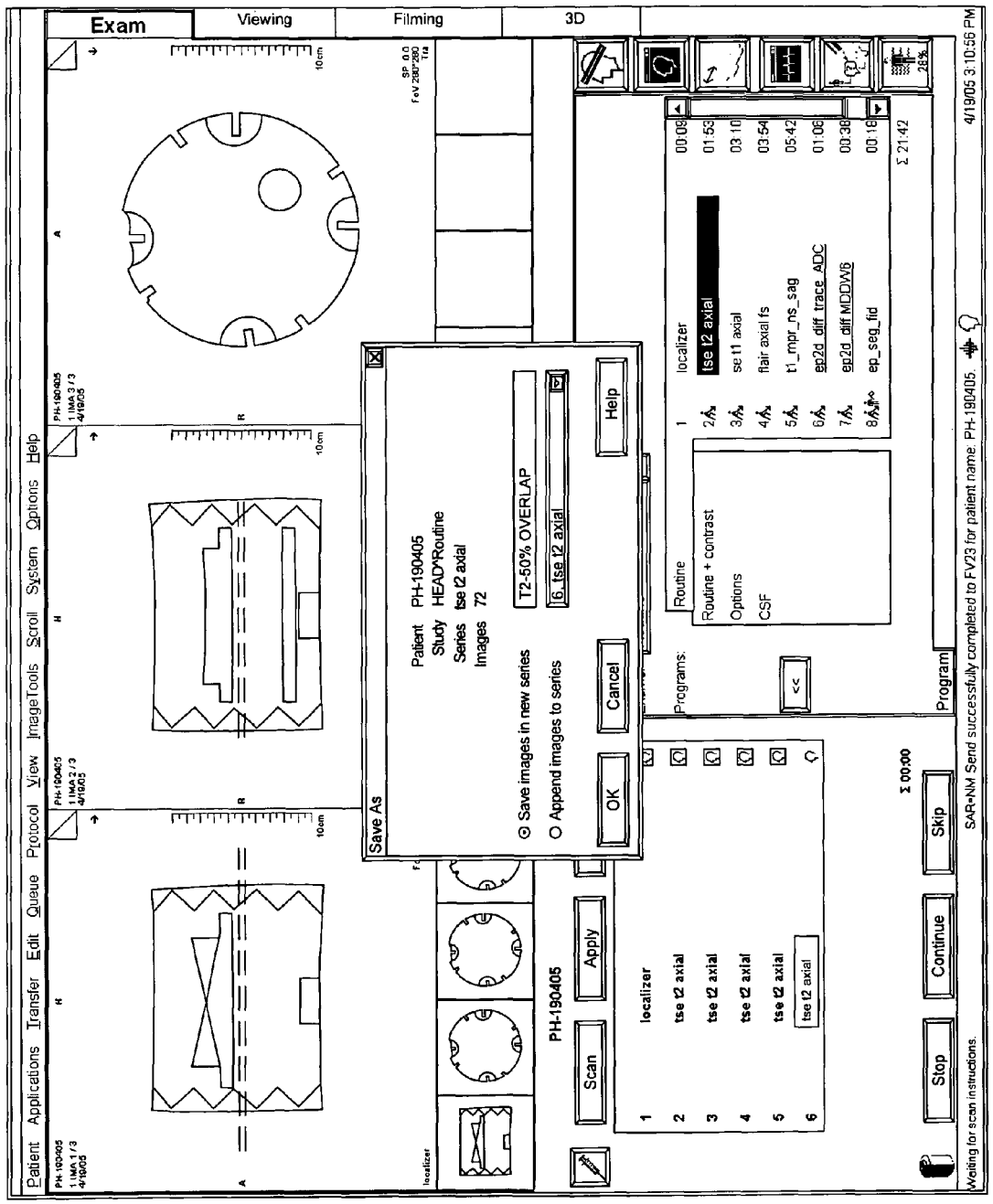

As stated above, the preferred embodiment can optionally be configured to acquire images in planes of any obliquity, which is believed to optimize visualization of the anatomy being scanned. This feature can preferably be achieved under user or software control by a parameter change in the chosen image acquisition protocol, which is believed to be possible with any conventional 2D sequence. Upon opening the sequence, the number of slices, the slice thickness and the orientation (i.e. obliquity) of the slices is assigned, as with any 2D sequence, off of a localizer image obtained in the axial, sagittal or coronal plane. The trajectory of the slices is then assigned by simply rotating, from a console for the imaging system using the available input commands to the system, the reference lines (indicating the trajectory of the slices) to a desired obliquity by an appropriate user input (e.g., a left mouse click and hold) (see FIG. 8(a)). It should be noted that the instructions provided herein are as per the preferred Siemens scanner, but the methodology described therefor can be readily applied to other scanners. Next, the "position" parameter under the exam card of the sequence is selected and the position "mode" selected to be "offcenter-shift." (see FIG. 8(b)). FIG. 8(b) shows the obliquity as a transverse image, but the line 800 defining the plane of acquisition can be dragged and changed to any orientation by appropriate user or software action (such as left mouse clicking on line 800 and manipulating line 800 to the desired obliquity). Once line 800 is positioned as desired, subsequent series will be oriented according to the plane defined line 800 with the shifted positions applied to that prescribed oblique plane. The selection of "offcenter-shift" as shown in FIG. 8(b) is in contrast to the only other option under position mode, i.e. "L-P-H" (which stands for Left, Posterior and Head, corresponding to the coronal, sagittal and axial planes respectively, relative to the table) as originally described. The "offcenter-shift" mode instructs the scanner to orient subsequent position shifts in the obliquity of the prescribed slices rather than in the coronal, sagittal, and axial plane relative to the table. After the first acquisition is complete (see FIG. 8(c)), subsequent acquisitions are prescribed by changing the position shift parameter only by 1 mm or 2 mm depending on the desired net overlap (that is, 1 mm for 100% and 2 mm for 50% (where slice thickness n equals 4 mm)), as shown in FIGS. 8(d)-(f), which depict 2 mm increments. This will yield 4 separate series for 50% overlap (see FIG. 8(g)) and 8 separate series for 100% overlap. The series can then be combined and interleaved accordingly by selecting (e.g., by a left mouse click) each series icon (representing each series) while pressing the control key, selecting "select series" under the "edit" menu (see FIG. 8(h)) and selecting "save as" under file (see FIG. 8(i)). The total number of images of this composite series will appear. The user should make sure that the composite series includes the correct number of images i.e. four times that of each individual series (for a four series overlap) and eight times that of each individual series (for an eight series overlap). In the example of FIGS. 3(a)-(d), the composite data file will be made up of 4*4 slices (i.e., 4 series of 4 slices each, or 16 slices). In the example of FIGS. 4(a)-(g), the composite data file will be made up of 8*x (i.e., 8 series of x slices each). The composite series is then named (see FIG. 8(j)). Before saving the named series, it is important to ensure that the preset sorting under the patient file is set at "slice position" (see FIG. 8(k) as indicated by the white arrow). Acquiring the 2D images in the plane of the desired 3D reconstruction, is believed to optimize the resolution of the 3D images. As such, it is preferred that the user define the plane of acquisition to be the same as the plane of desired 3D reconstruction.

The number of series will also depend on the desired overlap. In order to yield a 50% overlap, four separate series should be acquired and overlapped into a composite data set (see FIGS. 3(a)-(d)). The composite data set will have 4 times the number of images as each individual series, but because the images are overlapped by 50%, the data set appears re-segmented into a smaller slice thickness also defined by n/k. Starting with a 4 mm slice thickness, a 50% overlap will result in the composite data file having an effective slice thickness of 2 mm. Recent experiments suggest that the slice thickness remains at 4 mm but the distance between slices in the composite series is shortened such that the slices appear "thinner"

to the naked eye. In order to yield a 100% overlap, eight separate series should be acquired and overlapped (see FIGS. 4(a)-(h)). Starting from a 4 mm slice thickness, a 100% overlap will result in the composite data file having an effective slice thickness of 1 mm. Again, a 4 mm slice thickness facilitates these mathematical calculations, but as noted, other slice thickness values can be used.

At step 204, the scanner 102 thereafter acquires the next image data series starting from the adjusted starting table position. FIG. 3(b) illustrates the result of step 204 when a 50% overlap is desired, with 4 image slices being acquired for series 2 (the currently acquired series being indicated in boldface) starting from TP(0.5 n mm).

The flow of FIG. 2 will return to steps 202 and 204 depending upon the user's desired amount of overlap (step 206). With a desired 50% overlap, the flow of FIG. 2 will return twice more to steps 202 and 204 to yield the results shown in FIGS. 3(c) and 3(d). With a desired 100% overlap, the flow of FIG. 2 will return to steps 202 and 204 six more times to yield the results shown in FIGS. 4(c)-(h).

Once all image data series are acquired, at step 208, the control computer 104 preferably compiles all of the acquired slices for the plurality of series into a composite data file. This requires instructions to the control computer 104 as set forth in connection with FIGS. 8(g)-(k).

Figure 8K:
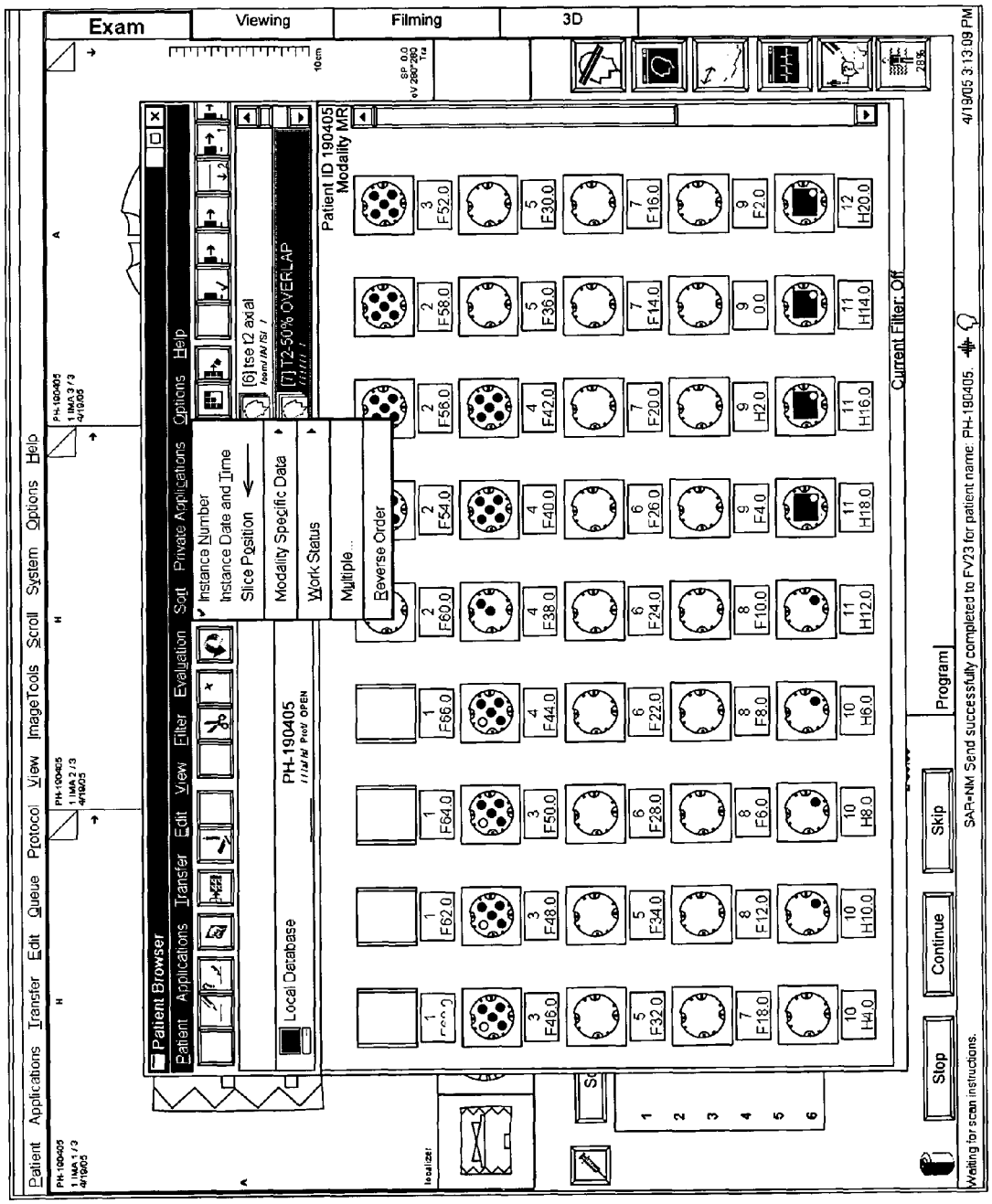

Experiments show that in order to assure proper interleaving the new composite series must be resorted (step 210). The scanner by default will be set to sort by "instance" which means images are sorted sequentially and anatomically. In order for RIOT to work, images need to be sorted by slice position. To do this manually, "Browser" is selected under the Patient file. "Local Database" is highlighted. The patient name and the composite sequence are then highlighted. "Slice position" is selected under the Sort file, as shown in FIG. 8(k). To ensure that the file remains correctly sorted, it is recommended that it be saved as described above under a new name. Experimentation indicates that although conventional sorting features available on computers 104 for scanner 102 can properly interleave slices by table position, the multiple steps involved may result in error. Should it be necessary, software modifications for scanner computer 104 to properly sort and interleave slices by table position are readily within the skill of a person having ordinary skill in the art following the teachings herein as explained below in connection with FIG. 9. Once the slices within the composite data file are preferably stored by slice position/table position (step 210), the computer 104 will interleave and overlap the series such that not only are the gaps of data filled, but the data is re-segmented giving the appearance of thinner slices. The slice thickness of the composite data set depends on the original slice thickness as well as # of series interleaved and is also defined as n/k. As noted above, the thickness of a composite series of four, each obtained at 4 mm slice thickness will be 2 mm (or 50% of the original slice thickness). In a 100% overlap instance, the composite series will be re-segmented into 25% of the original 4 mm slice thickness, or 1 m (see FIG. 4(h)). Therefore, the slice thickness goes from n mm to n/k mm. One hundred percent overlap is currently not believed to be possible even with multi-detector CT technology. As mentioned above, in reality, a 50% overlap will be more than enough for most 3D reconstructions.

Mathematical analysis of the composite data set shows that the re-segmented thinner slices are the result of approximations. The mathematical appendix appended hereto illustrates the mathematical validity of this re-segmenting process. To assure exact segmentation, software modifications for scanner computer 104 will be necessary. This is readily within the skill of a person having ordinary skill in the art.

Thereafter, the composite data file can be exported to 3D graphics rendering software (not shown) for display of MPRs and/or 3D reconstructions. An example of a suitable 3D rendering software package is the Voxar Site-wide 3D™ package produced by Voxar Limited of Edinburgh, Scotland. It is believed that software modifications may be necessary with some 3D rendering programs to ensure that the integrity of the composite data file is maintained upon loading. Such software modifications are believed to be well within the skill of a person having ordinary skill in the art.

It is worth noting that steps 200-210 of FIG. 2 can be performed with manual intervention by the clinician between each series acquisition as explained above to define the parameters for the next series acquisition. Alternatively, steps 200-210 can be performed automatically by the scanner control computer 104 without human intervention after invocation by a clinician of the start of the process. For example, steps 200-210 can be implemented in a software program executed by control computer 104 after invocation of a "macro" function or the like by the clinician through a control computer user interface. This software program could be configured to emulate the user input described in connection with FIGS. 8(a)-(k).

To invoke such an automated function, the clinician may be prompted to provide starting acquisition parameters such as image data series slice thickness, skip, the desired degree of overlap, starting table position, the plane of acquisition, etc. Once the staring parameters are specified, the software can automatically compute table position adjustments for subsequently acquired image series and automatically communicate control instructions to the scanner for acquiring each image series.

Alternatively, rather than requiring a user to provide initial acquisition parameters, a plurality of appropriately named predefined macro functions, each with its own predefined acquisition parameters, can be made available for invocation by the clinician from the control computer user interface.

Figure 9:
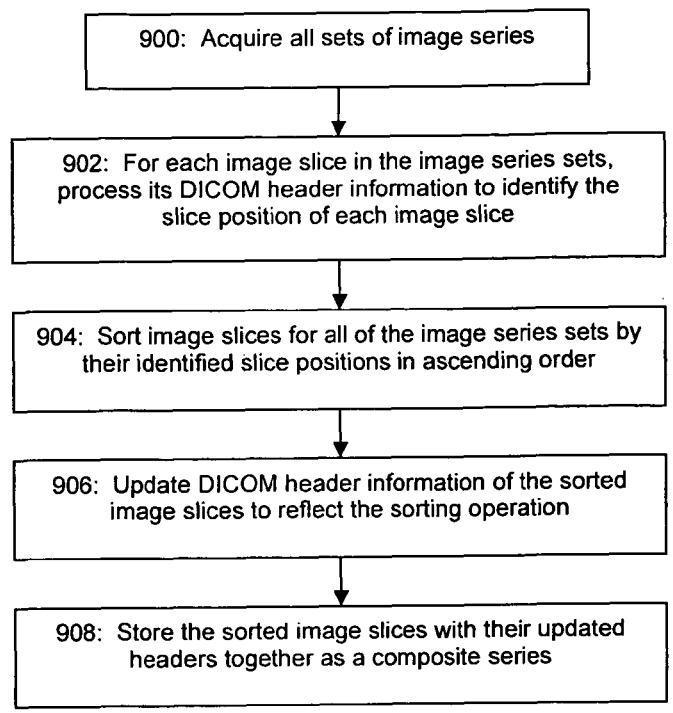
FIG. 9 depicts an exemplary preferred algorithm for sorting image slices by slice position.

The software program can also be configured to automatically perform the task of sorting the image slices in the composite data set into order by slice position. FIG. 9 depicts a flowchart for this sorting algorithm. The sorting operation preferably begins when all of the image slices for each of the acquired image series are obtained (step 900). When programmed on a conventional MRI scanner, the RIOT technique produces T output image series (usually $3 \leq T \leq 5$, but this need not be the case) each containing M images. Next, the software processes the header information for these slices to identify the slice position for each image slice (step 902). To produce the RIOT effect, the image slices in these series are preferably sorted in ascending order by their identified slice positions (step 904), relabeled as a single RIOT image series of length T*M (step 906) and stored in memory as a single image series (step 908).

Virtually all contemporary medical image data acquisition systems format images use the Digital Image Communications in Medicine (DICOM) standard. DICOM image objects are formatted according to this well-known standard to include a header elements and image picture elements (pixels). For the purposes of explaining the preferred sorting software, the header consists of a set of known descriptive elements or attributes that are encoded according to the standard as a tag-value pair. By correctly interpreting and processing the DICOM headers of the image slices, it is possible to adjust the image description attributes contained in each image slice to achieve the desired RIOT result.

As explained above, the sorting algorithm of FIG. 9 operates to read the header of each DICOM image comprising the T original output series, extracts the relevant attributes by searching for the relevant DICOM tags, determines the correct sorted order and then updates the relevant DICOM tags so that a DICOM compliant display device which might receive the resulting RIOT image series would display and process the images in the most advantageous manner.

In order to accomplish the necessary RIOT sorting and series relabeling, the following DICOM image attributes may be used:

TABLE 1

DICOM Standard Data Elements which may be used to implement a RIOT Sorting Algorithm

| DICOM Attribute Tag | Data Element Description | Usage |
|---|---|---|
| 0020000e | REL Series Instance UID | Modified to indicate new RIOT series |
| 00200011 | REL Series Number | Renumbered to a single RIOT series |
| 00200013 | REL Image Number | Renumbered to indicate proper sort order |
| 00200032 | REL Image Position Patient | Used to determine relative slice position |
| 00200037 | REL Image Orientation (Patient) | Used to determine relative slice position |
| 00201041 | REL Slice Location | Used to determine relative slice position |
| 00080008 | ID Image Type | Modified to indicate the image has been edited |
| 00080018 | ID SOP Instance UID | Modified to indicate the image has been edited |

When any original DICOM image is edited or modified the DICOM standard defines a set of attributes that must be modified in order to indicate and track the changes. For these attributes that are not listed in Table 1 above, a person having ordinary skill in the art can make the appropriate modifications according to known DICOM conventions.

A possible embodiment of the sorting software described in connection with FIG. 9 would include a DICOM Storage Service Class Provider (SCP) module which would be addressable over a computer network by any imaging modality (scanner) that supports the DICOM communication protocol as an appropriate Storage Service Class User (SCU). This DICOM SCP software module would receive unsorted image series from the imaging modality and temporarily store them in a directory on a local storage device. The sorting software module would be invoked using standard programming means by the SCP module. The sorting module would read each DICOM format image, parse the header tags, locate and extract the relevant attributes, and store them in a table in computer memory along with the name of the file used to temporarily store the image on the local storage device. Once this table was sorted in ascending order of slice location, the relevant image header tags will be redefined so that image slices are numbered sequentially by slice location, and the number of image series is set to 1. These modified image attributes are then written into the appropriate image file overwriting the previous values. Once the images are thus modified a final software module, a DICOM Storage SCU, is invoked to transfer the images to the desired destination (normally a permanent storage device or image display workstation) via the DICOM communication protocol.

In terms of time, it is believed that, with RIOT, each individual series can be acquired more rapidly than a single series acquired with 0% skip by conventional techniques. This speed is the result of utilizing a 100% skip instead of the conventional 0-20% skip. The total acquisition time for 4 series (regardless of the sequence) is believed to be less than that of any high resolution volumetric sequence. The total acquisition time of 8 series will be similar to that of a high resolution volumetric sequence (for most sequences). However, experimentation indicates that the total acquisition times are dramatically reduced using an ultra fast sequence such as True-FISP. In fact, the True-FISP sequence is the preferred sequence for most reconstructions as it displays high resolution despite its fast acquisition time.

Figure 7B:
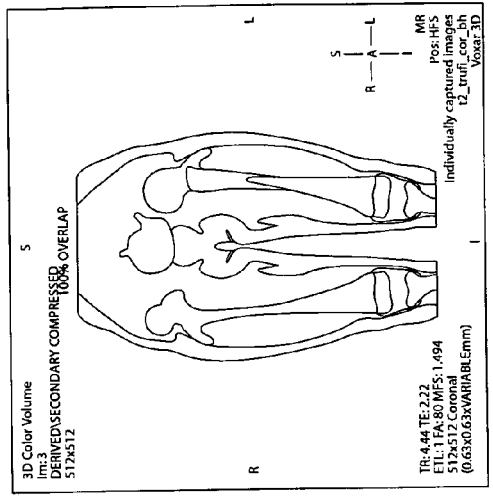
FIGS. 7(a) and (b) illustrate 3D and MPR's of the lower extremities of a patient applying RIOT to True-FISP sequence with 100% overlap.
Figure 7A:
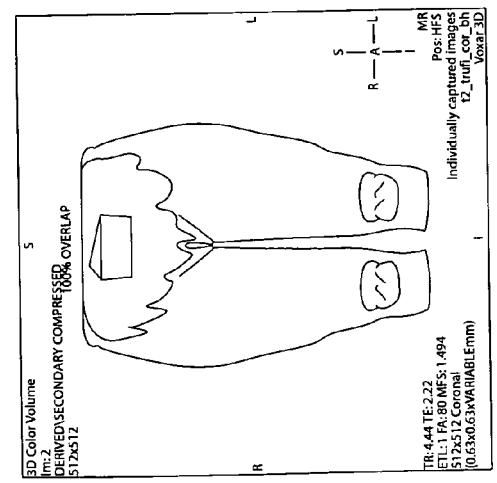

FIGS. 5($a$)-($d$) depict a 3D reconstruction derived from phantom images utilizing a True-FISP sequence for a (1) conventional non-RIOT sequence with 4 mm slice thickness and a 0% skip (FIG. 5($a$)), (2) two interleaved RIOT series, with slices having a 4 mm slice thickness and a 100% skip (FIG. 5($b$)); (3) four interleaved RIOT series, with slices having a 4 mm slice thickness and a 100% skip (FIG. 5($c$)); and (4) eight interleaved RIOT series, with slices having a 4 mm slice thickness and a 100% skip (FIG. 5($d$)). FIG. 7($a$) depicts a 3D reconstruction for True-FISP RIOT data acquired with a 100% overlap. FIG. 7($b$) depicts a coronal MPR for True-FISP RIOT data acquired with a 100% overlap.

Figure 6:
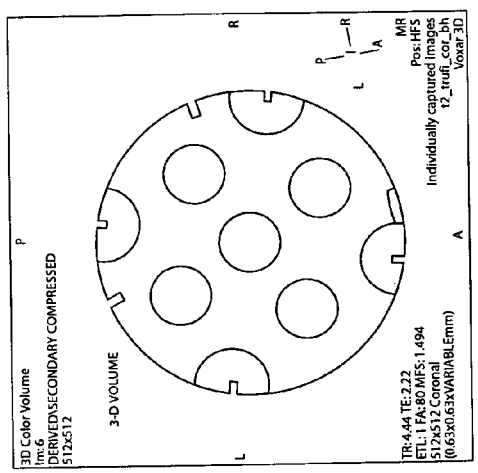
FIG. 6 illustrates a 3D image derived from a high resolution 3D sequence (3D Vibe)

With True-FISP, the total time required to acquire 8 series through an adult knee is 3 minutes. A high resolution volumetric sequence such as 3-D Vibe (see FIG. 6 for a 3D-Vibe sequence of a phantom) will take approximately 15 minutes. Depending on the pathology, a longer sequence, such as a T1-weighted sequence, may be indicated for better definition. However, as stated earlier, RIOT may be applied to any 2D sequence technique.

Although RIOT was conceived for the purpose of improving 3-D and multi-planar reconstructions, its impact on cross-sectional imaging is also believed to be profound. The reason for this is that because each individual series is acquired with a 100% gap between slices, "cross-talk" (which results in decreased SNR with thinner slices in conventional sequences), is no longer an issue. Using conventional non-RIOT techniques, slice thicknesses less than 2.5 mm will exhibit poor SNR, at times rendering images non-diagnostic. RIOT allows for even thinner slice reconfigurations (i.e., 1 mm). In addition, some sequences will not allow slice thicknesses below a certain value due to SAR limitations. With RIOT, thinner slices will not result in increased SAR, regardless of the sequence. This is due to the fact that the thinner slices are not acquired contiguously, (i.e. in one series). The result is improved resolution without loss of SNR (unlike with conventional 2-D and volumetric sequences). As noted, with RIOT, 4 series, each acquired at 4 mm, slices can be reconfigured into a single series segmented at 2 mm thick slices with a 50% overlap. Likewise, 8 such series can also be reconfigured into a single series segmented into 1 mm thick slices with 100% overlap, without sacrificing SNR. The thinner slices of the composite data sets will have identical SNR as the original data sets. Therefore, RIOT allows for thinner slices with both excellent resolution and excellent SNR. This will yield 3D reconstructions that surpass those of high resolution volumetric sequences (see FIGS. 5($c$), ($d$), 6, 7($a$)). Experimentation also indicates that MPR's and 3D images generated from just two interleaved series, each acquired with 4 mm thick slices and 100% gap (which in effect yields a series of 4 mm thick slices, with 0 skip and zero overlap), exhibit better resolution and SNR than those generated using the same sequence with the same slice thickness and 0 skip (compare FIGS. 5(*a*) and (*b*)). Yet, the acquisition time for both techniques is identical. Therefore, it is believed that RIOT will also improve the diagnostic quality of cross-sectional images, which is especially important when focusing on detailed structures.

It is worth noting that although RIOT is believed to enhance the inherent capability of any 2D sequence in terms of resolution and SNR, it is not believe that RIOT will overcome limitations inherent to a particular sequence (such as chemical shift artifact).

The present invention is also believed to be suitable for use with CT scanners. CT experimentation for RIOT was carried out with scans performed on a Siemens Sensations 16 row detector CT scanner manufactured by Siemens Medical Systems of Erlangen, Germany. Two CT data sets of 2×1 mm were generated from a CT data set acquired with 1.5 mm collimation at 5 mm slice thickness. The starting position of the second data set was 1 mm below the first. Both series were combined into a composite data set sorted by TP to yield a single data set of 1×1 mm with 100% overlap. This preliminary data suggests that interleaving may be possible with CT. It is believed that the application of RIOT to CT will result in even higher quality imaging than is currently possible with existing multi-detector technology.

In summary, RIOT allows for much higher quality 2D as well as MPR and 3D images with relatively little time cost. More importantly, it can be applied to most MR sequences (all except volumetric acquisitions). Accordingly, it is believed that RIOT can improve MR imaging overall whether 2D or 3D image sets. Finally, and most importantly, it is believed that RIOT will increase diagnostic accuracy, particularly when dealing with small anatomy which could particularly advantageously impact pediatric MR imaging.

While the present invention has been described above in relation to its preferred embodiment, various modifications may be made thereto that still fall within the invention's scope, as would be recognized by those of ordinary skill in the art. For example, in the preferred embodiment where 4 mm slices were acquired via RIOT to achieve a 50% overlap, series 1 was acquired beginning at a initial table position of TP(0 mm), series 2 was acquired beginning at a initial table position of TP(2 mm), series 3 was acquired beginning at a initial table position of TP(4 mm), and series 4 was acquired beginning at a initial table position of TP(6 mm). However, the nature of initial table position adjustments need not necessarily be sequential. For example, series 2 can be acquired beginning at a initial table position of TP(4 mm), series 3 can be acquired beginning at a initial table position of TP(6 mm), and series 4 can be acquired beginning at a initial table position of TP(2 mm). Moreover, the examples given herein are described in terms of a 50% overlap (4 image series) or a 100% overlap (8 image series), but it should be noted that other overlap percentages (e.g., 200%) could also be used in the practice or RIOT. These and other modifications to the invention will be recognizable upon review of the teachings herein. As such, the full scope of the present invention is to be defined solely by the appended claims and their legal equivalents.

Mathematical Appendix:

Sampling theory is used to increase the slice resolution in imaging for the two most common methods of three-dimensional imaging—multi-slice 2D and 3D imaging. In this discussion, a methodology is outlined for using multi-slice 2D imaging to increase the spatial resolution without the corresponding decrease in measured signal.

Drawing on the mathematical framework in Haacke et al referenced above, the 2D image projected along z is $$p(x,y) = \int p(x,y,z) dz$$

Figure 10A:
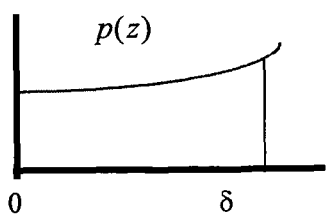
FIGS. 10(a) and (b) depict curve p(z)
Figure 10B:
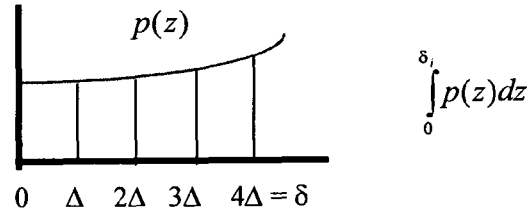

As shown in FIG. 10(*a*), the voxel value is the area under the curve of p(z) where δ is the thickness of the area to be examined under constant x and y $$p(x_0, y_0) = \int_0^\delta p(x_0, y_0, z) dz$$

where p(z) represents the distribution of the protons and it is assumed that p(z) is a well behaved function in the domain {0, δ} which we can partition (as shown in FIG. 10(*b*)) and then write the equation as $$S_i = \int_0^{\delta_1} p(z) dz$$
$$= \int_0^{1\Delta} p(z) dz + \int_{1\Delta}^{2\Delta} p(z) dz + \int_{2\Delta}^{3\Delta} p(z) dz + \int_{3\Delta}^{4\Delta} p(z) dz$$
$$= a_0^1 + a_1^2 + a_2^3 + a_3^4$$

Figure 11:
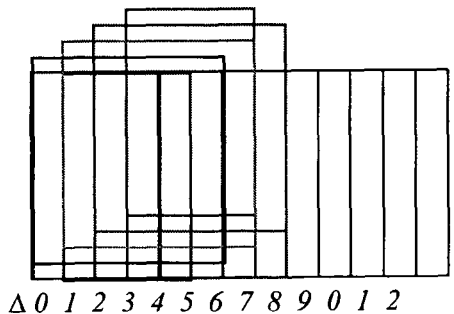
FIG. 11 depicts slices of thickness Δ.

This property can be used to overcome SAR and the slice thickness issue of SNR and resolution. To do this, a slice sequence is defined for a multi-slice measurement as follows (1, 3, 5 . . . ) and after the selected area of examination is completed, the region is re-scanned with a slice shift as shown below. Lets define $p_n$ for the voxel value at the $n^{th}$ slice and $a_i^j$ for the area under given by $$\int_{j\Delta}^{j\Delta} p(z) dz$$

as the voxel value for a slice of thickness Δ at position iΔ to jΔ. In FIG. 11, each segment is of length Δ and the thickness of each slice $S_i$ will vary from 4-6 Δ and have an offset from nΔ from the initial start position. To better illustrate the slices, they are depicted in FIG. 11 in different grayscale colors and slightly raised to show their relative positions.

The following linear system of equations can thus be generated:

$$S_0 = \int_0^{1\Delta} p(z)dz + \int_{1\Delta}^{2\Delta} p(z)dz + \int_{2\Delta}^{3\Delta} p(z)dz + \int_{3\Delta}^{4\Delta} p(z)dz$$
$$= a_0^1 + a_1^2 + a_2^3 + a_3^4$$

$$S_1 = \int_{1\Delta}^{2\Delta} p(z)dz + \int_{2\Delta}^{3\Delta} p(z)dz + \int_{3\Delta}^{4\Delta} p(z)dz + \int_{4\Delta}^{5\Delta} p(z)dz$$
$$= a_1^2 + a_2^3 + a_3^4 + a_4^5$$

$$S_2 = \int_{2\Delta}^{3\Delta} p(z)dz + \int_{3\Delta}^{4\Delta} p(z)dz + \int_{4\Delta}^{5\Delta} p(z)dz + \int_{5\Delta}^{6\Delta} p(z)dz$$
$$= a_2^3 + a_3^4 + a_4^5 + a_5^6$$

$$S_3 = \int_{3\Delta}^{4\Delta} p(z)dz + \int_{4\Delta}^{5\Delta} p(z)dz + \int_{5\Delta}^{6\Delta} p(z)dz + \int_{6\Delta}^{7\Delta} p(z)dz$$
$$= a_3^4 + a_4^5 + a_5^6 + a_6^7$$

-continued $$S_4 = \int_{4\Delta}^{5\Delta} p(z)dz + \int_{5\Delta}^{6\Delta} p(z)dz + \int_{6\Delta}^{7\Delta} p(z)dz + \int_{7\Delta}^{8\Delta} p(z)dz$$
$$= a_4^5 + a_5^6 + a_6^7 + a_7^8$$

$$S_5 = \int_{2\Delta}^{3\Delta} p(z)dz + \int_{3\Delta}^{4\Delta} p(z)dz + \int_{4\Delta}^{5\Delta} p(z)dz +$$
$$\int_{5\Delta}^{6\Delta} p(z)dz + \int_{6\Delta}^{7\Delta} p(z)dz$$
$$= a_2^3 + a_3^4 + a_4^5 + a_5^6 + a_6^7$$

$$S_6 = \int_{1\Delta}^{2\Delta} p(z)dz + \int_{2\Delta}^{3\Delta} p(z)dz + \int_{3\Delta}^{4\Delta} p(z)dz +$$
$$\int_{4\Delta}^{5\Delta} p(z)dz + \int_{5\Delta}^{6\Delta} p(z)dz$$
$$= a_1^2 + a_2^3 + a_3^4 + a_4^5 + a_5^6$$

$$S_7 = \int_{0}^{1\Delta} p(z)dz + \int_{1\Delta}^{2\Delta} p(z)dz + \int_{2\Delta}^{3\Delta} p(z)dz +$$
$$\int_{3\Delta}^{4\Delta} p(z)dz + \int_{4\Delta}^{5\Delta} p(z)dz$$
$$= a_0^1 + a_1^2 + a_2^3 + a_3^4 + a_4^5$$

that can be solved as follows:

$$\begin{bmatrix} 11110000 \\ 01111000 \\ 00111100 \\ 00011110 \\ 00001111 \\ 00111110 \\ 01111100 \\ 11111000 \end{bmatrix} \times \begin{bmatrix} a_0^1 \\ a_1^2 \\ a_2^3 \\ a_3^4 \\ a_4^5 \\ a_5^6 \\ a_6^7 \\ a_7^8 \end{bmatrix} = \begin{bmatrix} S_0 \\ S_1 \\ S_2 \\ S_3 \\ S_4 \\ S_5 \\ S_6 \\ S_7 \end{bmatrix}$$

which can be solved if the determinant of the matrix is not equal to zero. This operation will need to be done for each voxel and the number of slices and the slice shift needs to be selected such that the linear system of equations generated can be solved for the matrix of $a_i^j$. It should be noted that solution is not unique and various combinations of slice thickness and slice positions will yield results. This analytical solution is computationally intensive and various approximate solutions can be used to solve for the matrix of $a_i^j$.

What is claimed is:

1. A method of acquiring medical image data of a patient's region of interest, the method comprising:
    acquiring, by a magnetic resonance (MR) scanner, an image data series of a patient's region of interest starting from an initial table position in a coordinate system corresponding to a table position for the MR scanner, the image data series comprising a plurality of MR image slices, the image slices having a predetermined skip therebetween, each image slice having a predetermined slice thickness;
    repeating the acquiring step using the same image slice thickness and the same skip between image slices with an adjusted initial table position in the coordinate system until a desired degree of overlap between the plurality of acquired image data series is achieved;
    aggregating the plurality of image slices from the plurality of acquired image data series into a composite data file, wherein each image slice in the composite data file comprises header information; and
    automatically sorting the image slices in the composite data file by the table position at which each image slice was acquired by executing a software program configured to process each image slice's header information to identify how the image slices are to be sorted by the table position at which each image slice was acquired.

2. The method of claim 1 wherein the desired degree of overlap is 50%.

3. The method of claim 2 wherein the predetermined slice thickness is n mm, and wherein the adjusted initial table position between image data series is an adjustment of n/2 mm.

4. The method of claim 3 wherein n is approximately 4 mm.

5. The method of claim 3 wherein the predetermined skip between image slices is 100%.

6. The method of claim 1 wherein the desired degree of overlap is 100%.

7. The method of claim 6 wherein the predetermined slice thickness is n mm, and wherein the adjusted initial table position between image data series is an adjustment of n/4 mm.

8. The method of claim 1 further comprising generating a graphical display of a three-dimensional reconstruction of the patient's region of interest from the image slices within the composite data file.

9. The method of claim 1 further comprising generating a graphical display of a multi-planar reconstruction of the patient's region of interest from the image slices within the composite data file.

10. The method of claim 1 further comprising segmenting the sorted image slices in the composite data file to effectuate a thinner slice thickness for the image slices in the composite data file.

11. The method of claim 1 wherein the image data series are acquired along any one selected from the group consisting of an axial plane, a sagittal plane, and a coronal plane.

12. The method of claim 1 wherein the image data series is acquired along a user-selected plane of any obliquity.

13. The method of claim 12 wherein the image data series are acquired in a plane that is the same as a desired plane of 3D reconstruction.

14. A method of controlling a medical image scanner to acquire image slices of a patient's region of interest, the method comprising:
    instructing the scanner to acquire a first series of image slices starting from an initial table position TP(0) for the scanner, the image slices of the first series having a slice thickness of n mm and a predetermined skip therebetween;
    after the scanner acquires the first series of images slices, adjusting the initial table position to TP(n/k mm);
    instructing the scanner to acquire a next series of image slices starting from the adjusted initial table position, the image slices of the next series having the same slice thickness n and the same skip as the image slices of the first series; and
    repeating the adjusting step and the next series acquiring step until a desired degree of overlap is achieved, wherein the adjusting and the next series acquiring steps are repeated such that the table position is adjusted by units of n/k mm for each series, wherein the value of k is determined at least partially as a function of the desired degree of overlap.

15. The method of claim 14 wherein the desired degree of overlap is 50% and wherein k is 2.

16. The method of claim 14 wherein the desired degree of overlap is 100% and wherein k is 4.

17. The method of claim 14 wherein the medical image scanner is a magnetic resonance (MR) scanner.

18. The method of claim 14 wherein the medical image scanner is a computed tomography (CT) scanner.

19. The method of claim 14 further comprising aggregating the image slices from the plurality of acquired series into a composite data file.

20. The method of claim 19 further comprising sorting the image slices in the composite data file by the table position at which the image slices were acquired by the scanner.

21. The method of claim 20 wherein each image slice in the composite data file comprises header information, and wherein the sorting step comprises performing the sorting step automatically by a software program configured to process each image slice's header information to identify how the image slices are to be sorted by the table position at which each image slice was acquired.

22. The method of claim 14 wherein the image slices are acquired in an oblique plane.

23. The method of claim 22 wherein the oblique plane is a user-selected oblique plane.

24. The method of claim 23 wherein the user-selected oblique plane is a user-selected plane of any obliquity.

25. The method of claim 23 wherein the user-selected oblique plane is the same as a plane of 3D reconstruction for the image slices.

26. The method of claim 22 wherein the oblique plane is the same as a plane of 3D reconstruction for the image slices.

27. A computer readable storage medium for processing a plurality of image slices of a region of interest (ROI) in a composite data file, each image slice having been acquired at a different table position, wherein the image slices in the composite data file are out of order in terms of the table position at which they were acquired, and wherein each image slice comprises header information, the computer readable storage medium comprising:
  a code segment executable by a processor and resident on the computer-readable storage medium for processing the header information of the slices to determine the table position at which each slice was acquired; and
  a code segment executable by a processor and resident on the computer-readable storage medium for sorting the image slices in the composite data file in order by each image slice's determined table position.

28. The computer readable storage medium of claim 27 wherein each image slice belongs to one of a plurality of image data series, each image data series comprising a plurality of image slices having the same slice thickness and being acquired by a scanner starting from an initial table position with a predetermined skip therebetween, wherein the same slice thickness and the same skip was used to acquire each image data series, but wherein each image data series was acquired with a different initial table position, the computer readable storage medium further comprising:
  a code segment executable by a processor and resident on the computer-readable storage medium for reassembling the sorted image slices in a composite data file; and
  a code segment executable by a processor and resident on the computer-readable storage medium for modifying each image slice's header information to reflect the sort order.

29. The computer readable storage medium of claim 28 wherein the image slice header information comprises DICOM header information, and wherein the sorting code segment is further configured to sort the image slices in the composite data file in ascending order by each image slice's determined table position.

30. A system for acquiring medical image data of a patient's region of interest (ROI), the system comprising:
  an image scanner for generating a plurality of image slices of a patient's ROI; and
  an image scanner controller in communication with the image scanner, the image scanner controller being configured to provide a plurality of instructions to the scanner that define how the scanner will acquire the image slices; and
  wherein the image scanner controller is configured to execute a software program, the software program being configured to (1) instruct the scanner perform an acquisition of an image data series of a patient's region of interest starting from an initial position in a coordinate system, the image data series comprising a plurality of image slices having a predetermined skip therebetween, each image slice having a predetermined slice thickness, and (2) further instruct the scanner to repeat the acquisition using the same image slice thickness and the same skip between image slices but with an adjusted initial position in the coordinate system until a desired degree of overlap between the plurality of acquired image data series is achieved.

31. The system of claim 30 wherein the controller is further configured to execute the software program in response to user input through a controller user interface, and wherein the user input comprises a user specification of the initial table position.

32. The system of claim 31 wherein the user input further comprises a user specification of data indicative of the desired degree of overlap.

33. The system of claim 31 wherein the user input further comprises a user specification of the predetermined slice thickness.

34. The system of claim 31 wherein the user input further comprises a user specification of a plane of acquisition for each of the image data series.

35. The system of claim 34 wherein the plane of acquisition comprises a plane of any user-selected obliquity.

36. The system of claim 30 wherein the software program is further configured to assemble the plurality of image slices from the plurality of acquired image data series into a composite data file.

37. The system of claim 36 wherein the software program is further configured to sort the image slices in the composite data file by the table position at which each image slice was acquired.

38. The system of claim 37 further comprising a software program executed by the controller for generating a graphical display of at least one selected from the group consisting of a three-dimensional reconstruction and a multi-planar reconstruction of the patient's ROI from the image slices within the composite data file.

39. The system of claim 30 wherein the scanner comprises a magnetic resonance (MR) scanner, and wherein the coordinate system position is a table position for the MR scanner.

40. The system of claim 30 wherein the predetermined slice thickness is n mm, and wherein the adjusted initial table position between image data series is an adjustment of n/k mm, wherein k is a value indicative of the desired degree of overlap.

41. The system of claim 40 wherein n is approximately 4 mm.

42. The system of claim 41 wherein k is a value equal to 2 or 4.

* * * * *